(12) United States Patent
Chun et al.

(10) Patent No.: US 9,534,075 B2
(45) Date of Patent: Jan. 3, 2017

(54) ISOCYANURATE EPOXY COMPOUND HAVING ALKOXYSILYL GROUP, METHOD OF PREPARING SAME, COMPOSITION INCLUDING SAME, CURED PRODUCT OF THE COMPOSITION, AND USE OF THE COMPOSITION

(71) Applicant: KOREA INSTITUTE OF INDUSTRIAL TECHNOLOGY, Cheonan (KR)

(72) Inventors: Hyun-Aee Chun, Seongnam (KR); Sang-Yong Tak, Busan (KR); Su-Jin Park, Ansan (KR); Yun-Ju Kim, Seoul (KR); Sung-Hwan Park, Gunpo (KR); Sook-Yeon Park, Gunpo (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 335 days.

(21) Appl. No.: 14/355,557

(22) PCT Filed: Nov. 1, 2012

(86) PCT No.: PCT/KR2012/009130
§ 371 (c)(1),
(2) Date: Apr. 30, 2014

(87) PCT Pub. No.: WO2013/066078
PCT Pub. Date: May 10, 2013

(65) Prior Publication Data
US 2014/0308527 A1 Oct. 16, 2014

(30) Foreign Application Priority Data

Nov. 1, 2011  (KR) .................. 10-2011-0113007
Nov. 1, 2012  (KR) .................. 10-2012-0122947

(51) Int. Cl.
| | |
|---|---|
| *C08G 59/30* | (2006.01) |
| *C08L 63/00* | (2006.01) |
| *C08K 3/36* | (2006.01) |
| *C08K 3/40* | (2006.01) |
| *C07F 7/08* | (2006.01) |
| *C07F 7/10* | (2006.01) |
| *C07F 7/18* | (2006.01) |
| *C07D 405/14* | (2006.01) |
| *C07D 251/32* | (2006.01) |
| *B32B 15/092* | (2006.01) |
| *C08K 7/14* | (2006.01) |

(52) U.S. Cl.
CPC .......... *C08G 59/306* (2013.01); *B32B 15/092* (2013.01); *C07D 251/32* (2013.01); *C07D 405/14* (2013.01); *C07F 7/0812* (2013.01); *C07F 7/10* (2013.01); *C07F 7/1836* (2013.01); *C08K 3/36* (2013.01); *C08K 7/14* (2013.01); *C08L 63/00* (2013.01); *Y10T 428/31529* (2015.04)

(58) Field of Classification Search
USPC ..... 428/411, 626; 257/632; 521/27; 544/221
See application file for complete search history.

(56) References Cited

U.S. PATENT DOCUMENTS

| | | | |
|---|---|---|---|
| 4,220,513 A | 9/1980 | Green et al. | |
| 4,292,151 A | 9/1981 | Inata et al. | |
| 4,498,957 A | 2/1985 | Sasaki et al. | |
| 4,759,978 A * | 7/1988 | Takata ................ | C08G 59/063 442/117 |
| 4,789,711 A | 12/1988 | Monnier et al. | |
| 4,923,912 A * | 5/1990 | Sasaki ............... | C08G 59/4085 523/435 |
| 5,300,588 A | 4/1994 | Shiobara et al. | |
| 5,336,786 A | 8/1994 | Shiobara et al. | |
| 6,087,513 A | 7/2000 | Liao et al. | |
| 7,785,715 B2 | 8/2010 | Tsumura et al. | |

(Continued)

FOREIGN PATENT DOCUMENTS

| | | |
|---|---|---|
| CN | 1293685 A | 2/2001 |
| CN | 1303382 A | 7/2001 |

(Continued)

OTHER PUBLICATIONS

Chinese Office Action for Chinese Patent Application No. 201280052291.8 dated Oct. 28, 2015.
Chinese Office Action for Chinese Patent Application No. 201380046568.0 dated Nov. 2, 2015.
Extended European Search Report for European Patent Application No. 13772355.7 dated Oct. 16, 2015.
Zhang et al., "Characterization of siliconized diallyl bisphenol A type epoxy resin and study on its curing properties", Chemistry and Adhesion, Jun. 28, 2006, pp. 369-371 & 375, vol. 28, No. 6, Huaxue Yu Nianhe Bianji Weiyuanhui.

(Continued)

*Primary Examiner* — Tae H Yoon

(57) ABSTRACT

Disclosed are an alkoxysilylated isocyanurate epoxy compound, a composite of which exhibiting low CTE and high glass transition temperature or Tg-less and/or a cured product of which exhibiting good flame retardant property, a method of preparing the same, a composition including the same, a cured product formed of the composition, and a use of the composition. An isocyanurate epoxy compound having an alkoxysilyl group and an epoxy group in a core; a method of manufacturing the epoxy compound by the epoxidation and alkoxysilylation of a starting material; an epoxy composition including the epoxy compound; and a cured product and a use thereof, are provided. A composite of the epoxy composition has improved bonding efficiency between alkoxysilyl group and filler and between alkoxysilyl groups, and has good heat resistance, low CTE, and high glass transition temperature or Tg-less. A cured product formed of the epoxy composition has good flame retardant property.

24 Claims, 7 Drawing Sheets

(56) References Cited

U.S. PATENT DOCUMENTS

| | | | | |
|---|---|---|---|---|
| 9,023,588 | B2* | 5/2015 | Nakajima | C07F 7/1836 430/272.1 |
| 2003/0078322 | A1 | 4/2003 | Honda et al. | |
| 2004/0166241 | A1 | 8/2004 | Gallo et al. | |
| 2004/0241331 | A1 | 12/2004 | Durairaj et al. | |
| 2006/0009577 | A1 | 1/2006 | Hara | |
| 2007/0100043 | A1 | 5/2007 | Shiono | |
| 2007/0282081 | A1 | 12/2007 | Ichiroku | |
| 2008/0221238 | A1 | 9/2008 | Su et al. | |
| 2008/0255354 | A1 | 10/2008 | Popp et al. | |
| 2009/0203822 | A1* | 8/2009 | Shiobara | C08G 77/388 524/267 |
| 2011/0082321 | A1 | 4/2011 | Sakurai et al. | |
| 2011/0143092 | A1 | 6/2011 | Asai et al. | |
| 2011/0319589 | A1 | 12/2011 | Takeyama et al. | |
| 2012/0041102 | A1 | 2/2012 | Chun et al. | |
| 2012/0153512 | A1 | 6/2012 | Sugimoto et al. | |
| 2012/0248498 | A1 | 10/2012 | Takenaka et al. | |
| 2012/0292487 | A1 | 11/2012 | Yukawa et al. | |
| 2012/0295199 | A1 | 11/2012 | Takeyama et al. | |
| 2012/0315765 | A1 | 12/2012 | Nakajima et al. | |
| 2015/0304639 | A1* | 10/2015 | Lin | B41M 3/003 345/419 |

FOREIGN PATENT DOCUMENTS

| | | |
|---|---|---|
| CN | 1784462 A | 7/2006 |
| CN | 101701058 A | 5/2010 |
| EP | 0 618 246 A2 | 10/1994 |
| EP | 1114834 A1 | 7/2001 |
| EP | 2 119 721 A1 | 11/2009 |
| EP | 2343597 A2 | 7/2011 |
| EP | 2 767 535 A2 | 8/2014 |
| JP | 61-272244 A | 12/1986 |
| JP | 62-050312 A | 3/1987 |
| JP | S62-292828 A | 12/1987 |
| JP | S63-280720 A | 11/1988 |
| JP | 06-345847 A | 12/1994 |
| JP | 07-258240 A | 10/1995 |
| JP | 08-193091 A | 7/1996 |
| JP | 2003-055435 A | 2/2003 |
| JP | 2003-141933 A | 5/2003 |
| JP | 2006-012784 A | 1/2006 |
| JP | 2006-137800 A | 6/2006 |
| JP | 2007-126496 A | 5/2007 |
| JP | 2010-003897 A | 1/2010 |
| JP | 2010-065161 A | 3/2010 |
| JP | 2010-520952 A | 6/2010 |
| JP | 2011-057755 A | 3/2011 |
| JP | 2011-208120 A | 10/2011 |
| JP | 2012-246422 A | 12/2012 |
| JP | 2012-246425 A | 12/2012 |
| KR | 10-0673630 B1 | 1/2007 |
| KR | 10-2007-0068299 A | 6/2007 |
| KR | 10-0886331 B1 | 3/2009 |
| KR | 10-0929380 B1 | 12/2009 |
| WO | WO 99/62894 A2 | 12/1999 |
| WO | WO 2010/092947 A1 | 8/2010 |
| WO | WO 2011/093188 A1 | 8/2011 |
| WO | WO 2011/093219 A1 | 8/2011 |
| WO | WO 2011/093236 A1 | 8/2011 |
| WO | WO2011/102470 * | 8/2011 |
| WO | WO 2011/102470 A1 | 8/2011 |
| WO | WO 2012/070637 A1 | 5/2012 |
| WO | WO 2013/180375 A1 | 12/2013 |

OTHER PUBLICATIONS

Lei Xue et al., "Precise Synthesis of Poly(silphenylenesiloxane)s with Epoxy Side Functional Groups by Tris (pentafluorophenyl)borane as a Catalyst", Polymer Journal, Mar. 5, 2007, pp. 379-388, vol. 39, No. 4, The Society of Polymer Science, Japan.

Extended European Search Report for European Patent Application No. 13796871.5 dated Dec. 9, 2015.

Tahseen Razzaq et al., "Investigating the Existence of Nonthermal/Specific Microwave Effects Using Silicon Carbide Heating Elements as Power Modulators", The Journal of Organic Chemistry, 2008, pp. 6321-6329, vol. 73, No. 16, American Chemical Society.

Chinese Office Action for CN Application No. 201280053687.4, dated May 20, 2015.

Nobuo Suzuki et al., "Concise Encyclopedia of Polymer Science and Engineering", Polymer Dictionary, 1994, pp. 455-456, Maruzen Inc., Japan.

Extended European Search Report for European Application No. 13813009.1 dated Feb. 12, 2016.

Tsung-Han Ho et al., "Modification of epoxy resin with siloxane containing phenol aralkyl epoxy resin for electronic encapsulation application" European Polymer Journal, 2001, pp. 267-274, vol. 37, Elsevier Science Ltd.

Barry Arkles, "Silane Coupling Agents: Connecting Across Boundaries", 2006, pp. 1-60, Gelest Inc., http//www.gelest.de/goods/pdf/couplingagents.pdf.

International Search Report for PCT/KR2012/009130 filed on Nov. 1, 2012.

* cited by examiner

ISOCYANURATE EPOXY COMPOUND HAVING ALKOXYSILYL GROUP, METHOD OF PREPARING SAME, COMPOSITION INCLUDING SAME, CURED PRODUCT OF THE COMPOSITION, AND USE OF THE COMPOSITION

TECHNICAL FIELD

The present invention relates to an isocyanurate epoxy compound having an alkoxysilyl group (hereinafter 'alkoxysilylated isocyanurate epoxy compound'), a composite of which exhibiting good heat resistance properties and/or a cured product exhibiting good flame retardant properties, a method of preparing the same, a composition including the same, a cured product formed of the composition, and a use of the composition. More particularly, the present invention relates to an alkoxysilylated isocyanurate epoxy compound, a composite of which exhibiting good heat resistance properties, in particular, exhibiting a low coefficient of thermal expansion (CTE) and a high glass transition temperature increasing effect (including a transition temperature less (Tg-less) compound, not having a glass transition temperature) and/or a cured product exhibiting good flame retardant properties and not requiring a separate coupling agent, a method of preparing the same, a composition including the same, a cured product including the composition, and a use of the composition.

BACKGROUND ART

The coefficient of thermal expansion (CTE) of a polymer material—specifically, a cured epoxy resin compound—is about 50 to 80 ppm/° C., significantly high, on the level of several to tens of times the CTE of a inorganic material such as a ceramic material or a metal, (for example, the CTE of silicon is 3 to 5 ppm/° C., and the CTE of copper is 17 ppm/° C.). Thus, when the polymer material is used along with the inorganic material or the metal in a semiconductor, a display, or the like, the properties and processability of the polymer material are remarkably limited due to the different CTEs of the polymer material and the inorganic material or the metal. In addition, during semiconductor packaging in which a silicon wafer and a polymer substrate are used side by side, or during a coating process in which a polymer film is coated with an inorganic shielding layer to impart gas barrier properties, product defects such as the crack formations in an inorganic layer, the warpage of a substrate, the peeling-off of a coating layer, the failure of a substrate, and the like, may be generated due to a large CTE-mismatch between constituent materials during processing and/or due to changes in service temperatures.

Because of the high CTE of the polymer material and the resultant dimensional change of the polymer material, the development of technologies such as next generation semiconductor substrates, printed circuit boards (PCBs), packaging, organic thin film transistors (OTFTs), and flexible display substrates may be limited. Particularly, at the current time, the industries of the semiconductor and PCB fields are facing challenges in the design of next generation parts requiring high degrees of integration, miniaturization, flexibility, performance, and the like, in securing processability and reliability in parts due to polymer materials having significantly high CTE compared to metal/ceramic materials. In other words, due to the high thermal expansion properties of the polymer material at processing temperatures, when the parts are manufactured, defects may be generated, processability may be limited, and the design of the parts and securing of processability and reliability therein may be objects of concern. Accordingly, improved thermal expansion properties or the dimensional stability of the polymer material are necessary in order to secure processability and reliability of electronic parts.

In general, in order to improve thermal expansion properties—i.e., to obtain a low CTE in a polymer material such as an epoxy compound, (1) a method of producing a composite of the epoxy compound with inorganic particles (an inorganic filler) and/or fibers and (2) a method of designing a novel epoxy compound having a decreased CTE have been used.

When the composite of the epoxy compound and the inorganic particles as the filler is formed in order to improve thermal expansion properties, a large amount of silica filler particles, having a size in the range of several tens of nm to several tens of μm is required to be used to obtain a CTE decrease effect. However, due to the presence of the large amount of inorganic particles, the processability and physical properties of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to semiconductor structure miniaturization. When a filler having a particle size of 1 μm or less is used, the decrease in fluidity (viscosity decrease) may be worsened. When inorganic particles having a large average particle diameter are used, the frequency of insufficient filling in the case of a composition including a resin and the inorganic particles may increase. While the CTE may largely decrease when a composition including an organic resin and a fiber as the filler is used, the CTE may still be high as compared to that of a silicon chip or the like.

As described above, the manufacturing of highly integrated and high performance electronic parts for next generation semiconductor substrates, PCBs, and the like may be limited due to the limitations in the composite technology of epoxy compounds. Thus, the development of a polymer composite having improved heat resistance properties— namely, a low CTE and a high glass transition temperature— is required to overcome the challenge of a lack of heat resistance properties due to a high CTE and processability of a common thermosetting polymer composite.

DISCLOSURE

Technical Problem

An embodiment of the present invention provides an alkoxysilylatedisocyanurate epoxy compound, a composite of which exhibiting good heat resistance properties, particularly low CTE and high glass transition temperature properties and/or a cured product of which exhibiting good flame retardant properties.

Another embodiment of the present invention provides a method of preparing an alkoxysilylatedisocyanurate epoxy compound, a composite of which exhibiting good heat resistance properties, particularly low CTE and high glass transition temperature properties and/or a cured product of which exhibiting good flame retardant properties.

Another embodiment of the present invention also provides an epoxy composition including an alkoxysilylated isocyanurate epoxy compound, a composite of which exhibiting good heat resistance properties, particularly low CTE and high glass transition temperature properties and/or a cured product of which exhibiting good flame retardant properties.

Further another embodiment of the present invention provides a cured product formed of an epoxy composition in accordance with an example embodiment, including an alkoxysilylated epoxy compound, a composite of which exhibiting good heat resistance properties, particularly low CTE and high glass transition temperature properties and/or a cured product of which exhibiting good flame retardant properties.

In addition, another embodiment of the present invention provides a use of an epoxy composition in accordance with an example embodiment.

Technical Solution

According to the first embodiment of the present invention, there is provided an isocyanurate epoxy compound having an alkoxysilyl group, a structure of which being illustrated by Formula 1,

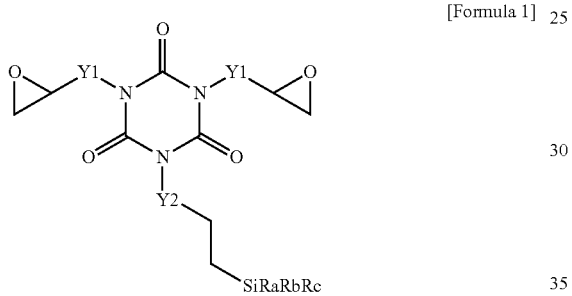

[Formula 1]

in Formula 1, where each of Y1 and Y2 is independently selected from the group consisting of a C1-C10 alkanediyl, a C6-C10 aryldiyl and a C7-C10 arylated alkanediyl group and may be the same or different. The alkanediyl group may be linear or branched, cyclic or acyclic, and the alkanediyl, the aryldiyl and the arylated alkanediyl group may or may not include a heteroatom of N, O, S or P.

At least one of $R_a$ to $R_c$ is a C1-C10 alkoxy group, and the remainders thereof are a C1-C10 alkyl, a C6-C10 aryl, or a C7-C10 aralkyl group. The alkyl group and the alkoxy group may be linear or branched and cyclic or acyclic, and the alkyl, the alkoxy, the aryl and the aralkyl group may or may not include a heteroatom of N, O, S or P.

According to the second embodiment of the present invention, the isocyanurate epoxy compound having an alkoxysilyl group of the first embodiment, in which Y1 is selected from the group consisting of the C1-C10 alkanediyl, the C6-C10 aryldiyl and the C7-C10 arylated alkanediyl group, and Y2 is selected from the group consisting of the C2-C10 alkanediyl, the C6-C10 aryldiyl and the C7-C10 arylated alkanediyl group, may be provided.

According to the third embodiment of the present invention, the isocyanurate epoxy compound having an alkoxysilyl group of the first embodiment, in which Y1 is selected from the group consisting of the C2-C10 alkanediyl, the C6-C10 aryldiyl and the C7-C10 arylated alkanediyl group, and Y2 is selected from the group consisting of the C1-C10 alkanediyl, the C6-C10 aryldiyl and the C7-C10 arylated alkanediyl group, may be provided.

According to the fourth embodiment of the present invention, the isocyanurate epoxy compound having an alkoxysilyl group of the first embodiment, in which Y1 is selected from the group consisting of the C2-C10 alkanediyl, the C6-C10 aryldiyl and the C7-C10 arylated alkanediyl group, and Y2 is selected from the group consisting of the C2-C10 alkanediyl, the C6-C10 aryldiyl and the C7-C10 arylated alkanediyl group, may be provided.

According to the fifth embodiment of the present invention, the isocyanurate epoxy compound having an alkoxysilyl group of the first embodiment, in which one of $R_a$ to $R_c$ is an ethoxy group, may be provided.

According to the sixth embodiment of the present invention, the isocyanurate epoxy compound having an alkoxysilyl group of the first embodiment, in which the isocyanurate epoxy compound having an alkoxysilyl group is one selected from the group consisting of the following Formulae (A) to (C), may be provided.

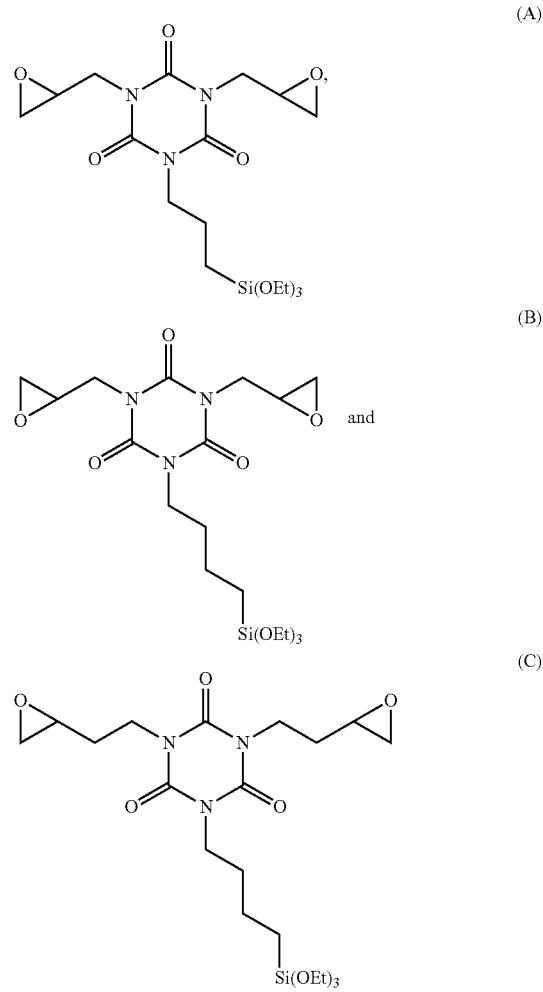

According to the seventh embodiment of the present invention, there is provided at least one compound selected from the group consisting of the following Formulae (D) to (F).

(D)
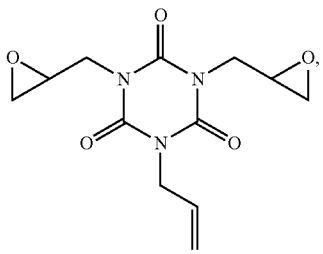

(E)
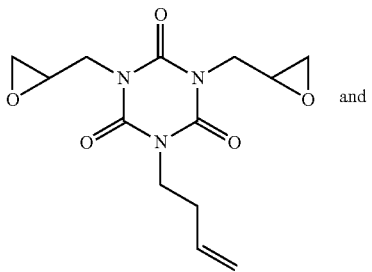
and (F)
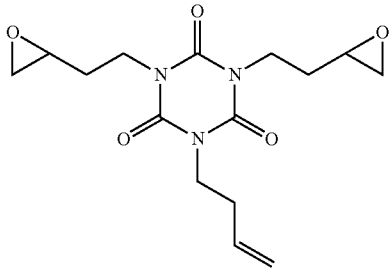

According to the eighth embodiment of the present invention, there is provided an isocyanurate epoxy polymer having an alkoxysilyl group of the following Formula 2,

[Formula 2]
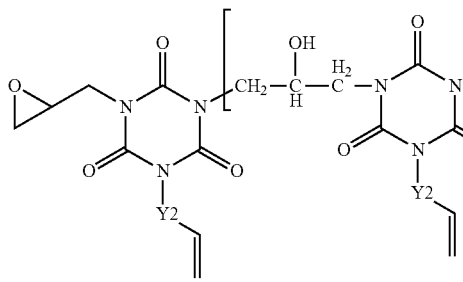

where Y2 is selected from the group consisting of a C1-C10 alkanediyl, a C6-C10 aryldiyl and a C7-C10 arylated alkanediyl group and may be the same or different. The alkanediyl group may be linear or branched and cyclic or acyclic, the alkanediyl, the aryldiyl and the arylated alkanediyl group may or may not include a heteroatom of N, O, S or P, and n is an integer from 0 to 100.

According to a ninth embodiment of the present invention, there is provided a method of preparing an isocyanurate epoxy compound having an alkoxysilyl group having a structure illustrated by Formula 1 including a first step of preparing a reaction intermediate having a structure illustrated by Formula 3 through the alkenylation and epoxidation of a compound having a structure illustrated by Formula 2-1 in the presence of a base, an optional catalyst and an optional solvent; and a second step of reacting the reaction intermediate of the Formula 3 with an alkoxysilane of the following Formula R2 in the presence of a metal catalyst and an optional solvent,

[Formula 1]
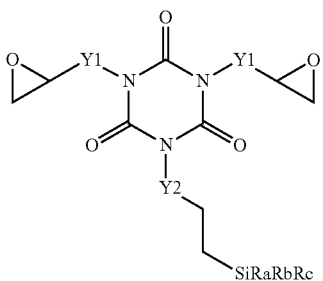

in Formula 1, where Y1 is —$CH_2$—; Y2 is selected from the group consisting of a C1-C10 alkanediyl, a C6-C10 aryldiyl and a C7-C10 arylated alkanediyl group. The alkanediyl group may be linear or branched and cyclic or acyclic, and the alkanediyl, the aryldiyl and the arylated alkanediyl group may or may not include a heteroatom of N, O, S or P.

At least one of $R_a$ to $R_c$ is a C1-C10 alkoxy group, and the remainders thereof are a C1-C10 alkyl, a C6-C10 aryl, or a C7-C10 aralkyl group. The alkyl group and the alkoxy group may be linear or branched and cyclic or acyclic, and the alkyl, the alkoxy, the aryl and the aralkyl group may or may not include a heteroatom of N, O, S or P,

[Formula 2-1]
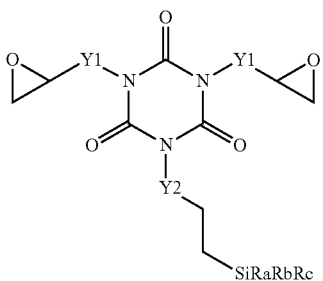

[Formula 3]

In Formula 3, where Y1 is —$CH_2$—; Y2 is selected from the group consisting of a C1-C10 alkanediyl, a C6-C10 aryldiyl and a C7-C10 arylated alkanediyl group. The alkanediyl group may be linear or branched, cyclic or acyclic, and the alkanediyl, the aryldiyl and the arylated alkanediyl group may or may not include a heteroatom of N, O, S or P, $HSiR_aR_bR_c$ [Formula R2]

in Formula R2, where at least one of $R_a$ to $R_c$ is a C1-C10 alkoxy group, and the remainders thereof are a C1-C10 alkyl, a C6-C10 aryl, or a C7-C10 aralkyl group. The alkoxy group and the alkyl group may be linear or branched and cyclic or acyclic, and the alkyl, the alkoxy, the aryl and the aralkyl group may or may not include a heteroatom of N, O, S or P.

According to the tenth embodiment of the present invention, the method of preparing an isocyanurate epoxy compound having an alkoxysilyl group of the ninth embodiment, in which the first step is an alkenylation reaction of the compound of the above Formula 2-1 and an alkenyl compound having a structure illustrated by Formula R1, and then by a subsequent epoxidation reaction with epichlorohydrin in situ, may be provided.

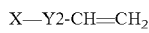 [Formula R1]

in Formula R1, where Y2 is selected from the group consisting of a C1-C10 alkanediyl, a C6-C10 aryldiyl and a C7-C10 arylated alkanediyl group. The alkanediyl group may be linear or branched and cyclic or acyclic, the alkanediyl, the aryldiyl and the arylated alkanediyl group may or may not include a heteroatom of N, O, S or P, and X may be Cl, Br, I, —O—SO$_2$—CH$_3$, —O—SO$_2$—CF$_3$, or —O—SO$_2$—C$_6$H$_4$—CH$_3$.

According to the eleventh embodiment of the present invention, the method of preparing an isocyanurate epoxy compound having an alkoxysilyl group of the ninth embodiment, in which the first step is conducted by the epoxidation reaction of the compound of the above Formula 2-1 with epichlorohydrin and the subsequent alkenylation reaction of the alkenyl compound having a structure illustrated by Formula R1 in situ, may be provided,

 [Formula R1]

in Formula R1, where Y2 is selected from the group consisting of a C1-C10 alkanediyl, a C6-C10 aryldiyl and a C7-C10 arylated alkanediyl group. The alkanediyl group may be linear or branched and cyclic or acyclic, the alkanediyl, the aryldiyl and the arylated alkanediyl group may or may not include a heteroatom of N, O, S or P, and X may be Cl, Br, I, —O—SO$_2$—CH$_3$, —O—SO$_2$—CF$_3$, or —O—SO$_2$—C$_6$H$_4$—CH$_3$.

According to a twelfth embodiment of the present invention, there is provided a method of preparing an isocyanurate epoxy compound having an alkoxysilyl group having a structure illustrated by Formula 1 including a first step of preparing a reaction intermediate having a structure illustrated by Formula 3 by reacting a compound having a structure illustrated by Formula 2-2 with a peroxide in the presence of an optional base and an optional solvent, and a second step of reacting the reaction intermediate of the above Formula 3 with an alkoxysilane having a structure illustrated by Formula R2 in the presence of a metal catalyst and an optional solvent,

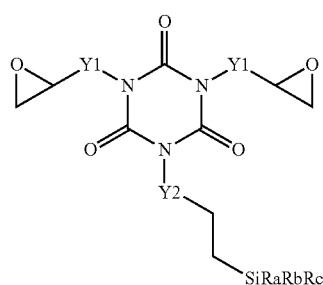

[Formula 1]

in Formula 1, where Y1 and Y2 are selected from the group consisting of a C1-C10 alkanediyl, a C6-C10 aryldiyl and a C7-C10 arylated alkanediyl group and may be the same or different. The alkanediyl group may be linear or branched and cyclic or acyclic, and the alkanediyl, the aryldiyl and the arylated alkanediyl group may or may not include a heteroatom of N, O, S or P.

At least one of R$_a$ to R$_c$ is a C1-C10 alkoxy group, and the remainders thereof are a C1-C10 alkyl, a C6-C10 aryl, or a C7-C10 aralkyl group. The alkyl group and the alkoxy group may be linear or branched and cyclic or acyclic, and the alkyl, the alkoxy, the aryl and the aralkyl group may or may not include a heteroatom of N, O, S or P,

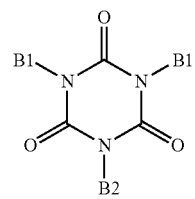

[Formula 2-2]

in Formula 2-2, where B1 is —Y1-CH=CH$_2$, B2 is —Y2-CH=CH$_2$, and Y1 and Y2 are selected from the group consisting of a C1-C10 alkanediyl, a C6-C10 aryldiyl and a C7-C10 arylated alkanediyl group and may be the same or different. The alkanediyl group may be linear or branched and cyclic or acyclic, and the alkanediyl, the aryldiyl and the arylated alkanediyl group may or may not include a heteroatom of N, O, S or P,

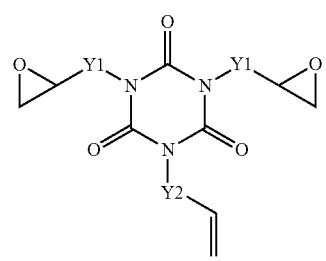

[Formula 3]

in Formula 3, where Y1 and Y2 are selected from the group consisting of a C1-C10 alkanediyl, a C6-C10 aryldiyl and a C7-C10 arylated alkanediyl and may be the same or different. The alkanediyl group may be linear or branched and cyclic or acyclic, and the alkanediyl, the aryldiyl and the arylated alkanediyl group may or may not include a heteroatom of N, O, S or P,

 [Formula R2]

in Formula R2, where at least one of R$_a$ to R$_c$ is a C1-C10 alkoxy group, and the remainders thereof are a C1-C10 alkyl, a C6-C10 aryl, or a C7-C10 aralkyl group. The alkoxy group and the alkyl group may be linear or branched and cyclic or acyclic, and the alkanediyl, the aryldiyl and the arylated alkanediyl group may or may not include a heteroatom of N, O, S or P.

According to the thirteenth embodiment of the present invention, the method of preparing an isocyanurate epoxy compound having an alkoxysilyl group of the twelfth embodiment, in which the compound of Formula 2-2 is prepared by reacting a compound having a structure illustrated by Formula 2-1 and the following alkenyl compound having a structure illustrated by Formula R1 in the presence of a base, an optional catalyst and an optional solvent, may be provided,

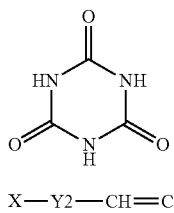

[Formula 2-1]

X—Y2—CH=CH$_2$     [Formula R1]

in Formula R1, where Y2 is selected from the group consisting of a C1-C10 alkanediyl, a C6-C10 aryldiyl and a C7-C10 arylated alkanediyl group. The alkanediyl group may be linear or branched and cyclic or acyclic, the alkanediyl, the aryldiyl and the arylated alkanediyl group may or may not include a heteroatom of N, O, S or P, and X may be Cl, Br, I, —O—SO$_2$—CH$_3$, —O—SO$_2$—CF$_3$, or —O—SO$_2$—C$_6$H$_4$—CH$_3$.

According to the fourteenth embodiment of the present invention, the method of preparing an isocyanurate epoxy compound having an alkoxysilyl group of the tenth embodiment, in which the first step is conducted by adding 0.3 to 5 equivalents of an alkenyl group of the above compound R1 with respect to 1 equivalent of an amine of the above compound 2-1, and subsequently adding 1 to 10 equivalents of epichlorohydrin with respect to 1 equivalent of the amine of the above compound 2-1 in situ, may be provided.

According to the fifteenth embodiment of the present invention, the method of preparing an isocyanurate epoxy compound having an alkoxysilyl group of the eleventh embodiment, in which the first step is conducted by adding 0.6 to 10 equivalents of epichlorohydrin with respect to 1 equivalent of an amine of the above compound 2-1, and subsequently adding 0.3 to 5 equivalents of an alkenyl group with respect to 1 equivalent of an amine of the above compound 2-1 in situ, may be provided.

According to the sixteenth embodiment of the present invention, the method of preparing an isocyanurate epoxy compound having an alkoxysilyl group of the ninth embodiment, in which the alkenylation is performed at room temperature to 150° C. for 1 to 24 hours, and the epoxidation is performed at room temperature to 150° C. for 1 to 24 hours, may be provided.

According to the seventeenth embodiment of the present invention, the method of preparing an isocyanurate epoxy compound having an alkoxysilyl group of the ninth embodiment, in which the base in the first step is selected from the group consisting of NaH, KOH, NaOH, K$_2$CO$_3$ and Na$_2$CO$_3$, may be provided.

According to the eighteenth embodiment of the present invention, the method of preparing an isocyanurate epoxy compound having an alkoxysilyl group of the ninth embodiment, in which the catalyst in the first step is selected from the group consisting of tetramethylammonium chloride, tetramethylammonium bromide, tetrabutylammonium iodide, trimethylbenzylammonium chloride, and triethylbenzylammonium chloride, may be provided.

According to the nineteenth embodiment of the present invention, the method of preparing an isocyanurate epoxy compound having an alkoxysilyl group of the ninth embodiment, in which the solvent in the first step is selected from the group consisting of 1,4-dioxane, acetonitrile, tetrahydrofuran (THF), dimethyl formamide (DMF), dimethyl sulfoxide (DMSO), methanol and ethanol, may be provided.

According to the twentieth embodiment of the present invention, the method of preparing an isocyanurate epoxy compound having an alkoxysilyl group of the twelfth embodiment, in which the first step is performed by reacting 1 to 5 equivalents of a peroxide group of the peroxide with respect to 1 equivalent of the alkenyl group of the above compound 2-2, may be provided.

According to the twenty-first embodiment of the present invention, the method of preparing an isocyanurate epoxy compound having an alkoxysilyl group of the twelfth embodiment, in which the peroxide in the first step is selected from the group consisting of meta-chloroperoxybenzoic acid (m-CPBA), H$_2$O$_2$, dimethyldioxirane (DMDO) and oxone, may be provided.

According to the twenty-second embodiment of the present invention, the method of preparing an isocyanurate epoxy compound having an alkoxysilyl group of the twelfth embodiment, in which the first step is performed at room temperature to 100° C. for 1 to 120 hours, may be provided.

According to the twenty-third embodiment of the present invention, the method of preparing an isocyanurate epoxy compound having an alkoxysilyl group of the twelfth embodiment, in which the optional base in the first step is selected from the group consisting of KOH, NaOH, K$_2$CO$_3$KHCO$_3$, NaH, triethylamine and diisopropylethylamine, may be provided.

According to the twenty-fourth embodiment of the present invention, the method of preparing an isocyanurate epoxy compound having an alkoxysilyl group of the twelfth embodiment, in which the solvent in the first step is at least one selected from the group consisting of THF, methyl ethyl ketone (MEK), DMF, DMSO, methylene chloride (MC) and chloroform, may be provided.

According to the twenty-fifth embodiment of the present invention, the method of preparing an isocyanurate epoxy compound having an alkoxysilyl group of the ninth or twelfth embodiment, in which the second step is performed by reacting 1 to 3 equivalents of alkoxysilane of the above compound R2 with respect to 1 equivalent of an alkenyl substituent of the reaction intermediate of the above compound 3, may be provided.

According to the twenty-sixth embodiment of the present invention, the method of preparing an isocyanurate epoxy compound having an alkoxysilyl group of the ninth or twelfth embodiment, in which the reaction in the second step is conducted at room temperature to 120° C. for 1 to 72 hours, may be provided.

According to the twenty-seventh embodiment of the present invention, the method of preparing an isocyanurate epoxy compound having an alkoxysilyl group of the ninth or twelfth embodiment, in which the metal catalyst in the second step is PtO$_2$ or H$_2$PtCl$_6$ (chloroplatinic acid), may be provided.

According to the twenty-eighth embodiment of the present invention, the method of preparing an isocyanurate epoxy compound having an alkoxysilyl group of the ninth or twelfth embodiment, in which the solvent in the second step is at least one selected from the group consisting of toluene, acetonitrile, THF, MEK, DMF, DMSO, and MC, may be provided.

According to the twenty-ninth embodiment of the present invention, there is provided an epoxy composition including an isocyanurate epoxy compound having an alkoxysilyl group having a structure illustrated by Formula 1,

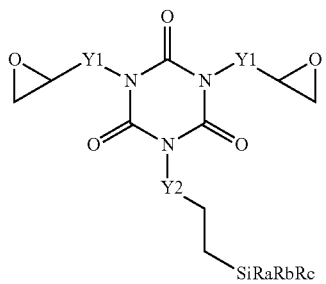

[Formula 1]

in Formula 1, where Y1 and Y2 are selected from the group consisting of a C1-C10 alkanediyl, a C6-C10 aryldiyl and a C7-C10 arylated alkanediyl group and may be the same or different. The alkanediyl group may be linear or branched and cyclic or acyclic, and the alkanediyl, the aryldiyl and the arylated alkanediyl group may or may not include a heteroatom of N, O, S or P.

At least one of $R_a$ to $R_c$ is a C1-C10 alkoxy group, and the remainders thereof are a C1-C10 alkyl, a C6-C10 aryl, or a C7-C10 aralkyl group. The alkyl group and the alkoxy group may be linear or branched and cyclic or acyclic, and the alkyl, the alkoxy, the aryl and the aralkyl group may or may not include a heteroatom of N, O, S or P.

According to the thirtieth embodiment of the present invention, the epoxy composition of the twenty-ninth embodiment, further including at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound, may be provided.

According to the thirty-first embodiment of the present invention, the epoxy composition of the thirty embodiment, in which the epoxy compound includes bisphenol A, bisphenol F, bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic or a novolak unit, as a core structure, may be provided.

According to the thirty-second embodiment of the present invention, the epoxy composition of the thirty-first embodiment, in which the epoxy compound includes the bisphenol A, the biphenyl, the naphthalene or the fluorene, as the core structure, may be provided.

According to the thirty-third embodiment of the present invention, the epoxy composition according to any one of the twenty-ninth embodiment to the thirty-second embodiment, in which the epoxy composition includes 10 wt % to 100 wt % of the isocyanurate epoxy compound having an alkoxysilyl group and 0 wt % to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the thirty-fourth embodiment of the present invention, the epoxy composition of the thirty-third embodiment, in which the epoxy composition includes 30 wt % to 100 wt % of the isocyanurate epoxy compound having an alkoxysilyl group and 0 wt % to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the thirty-fifth embodiment of the present invention, there is provided an epoxy composition including an isocyanurate epoxy compound having an alkoxysilyl group having a structure illustrated by Formula 1 and a curing agent,

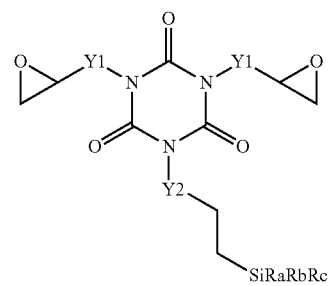

[Formula 1]

in Formula 1, where Y1 and Y2 are selected from the group consisting of a C1-C10 alkanediyl, a C6-C10 aryldiyl and a C7-C10 arylated alkanediyl and may be the same or different. The alkanediyl group may be linear or branched and cyclic or acyclic, and the alkanediyl, the aryldiyl and the arylated alkanediyl group may or may not include a heteroatom of N, O, S or P.

At least one of $R_a$ to $R_c$ is a C1-C10 alkoxy group, and the remainders thereof are a C1-C10 alkyl, a C6-C10 aryl, or a C7-C10 aralkyl group. The alkyl group and the alkoxy group may be linear or branched and cyclic or acyclic, and the alkyl, the alkoxy, the aryl and the aralkyl group may or may not include a heteroatom of N, O, S or P.)

According to the thirty-sixth embodiment of the present invention, the epoxy composition of the thirty-fifth embodiment, further including at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound, may be provided.

According to the thirty-seventh embodiment of the present invention, the epoxy composition of the thirty-sixth embodiment, in which the epoxy compound includes bisphenol A, bisphenol F, bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic or a novolak unit, as a core structure, may be provided.

According to the thirty-eighth embodiment of the present invention, the epoxy composition of the thirty-seventh embodiment, in which the epoxy compound includes the bisphenol A, the biphenyl, the naphthalene or the fluorene, as the core structure, may be provided.

According to the thirty-ninth embodiment of the present invention, the epoxy composition according to any one of the thirty-fifth embodiment to the thirty-eighth embodiment, in which the epoxy composition includes 10 wt % to 100 wt % of the isocyanurate epoxy compound having an alkoxysilyl group and 0 wt % to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the fortieth embodiment of the present invention, the epoxy composition of the thirty-ninth embodiment, in which the epoxy composition includes 30 wt % to 100 wt % of the isocyanurate epoxy compound having an alkoxysilyl group and 0 wt % to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the forty-first embodiment of the present invention, the epoxy composition according to any one of the twenty-ninth embodiment to the fortieth embodiment, further including a curing accelerator, may be provided.

According to the forty-second embodiment of the present invention, the epoxy composition according to any one of the twenty-ninth embodiment to the forty-first embodiment, further including inorganic particles or a fiber, may be provided.

According to the forty-third embodiment of the present invention, the epoxy composition of the forty-second embodiment, further including the inorganic particles when the epoxy composition includes the fiber, may be provided.

According to the forty-fourth embodiment of the present invention, the epoxy composition of the forty-second embodiment or the forty-third embodiment, in which the inorganic particle is at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane, may be provided.

According to the forty-fifth embodiment of the present invention, the epoxy composition of the forty-second embodiment, in which an amount of the inorganic particles in the epoxy composition is 5 wt % to 95 wt % based on a total amount of the epoxy composition, may be provided.

According to the forty-sixth embodiment of the present invention, the epoxy composition of the forty-fifth embodiment, in which an amount of the inorganic particles is 30 wt % to 95 wt % based on a total amount of the epoxy composition, may be provided.

According to the forty-seventh embodiment of the present invention, the epoxy composition of the forty-sixth embodiment, in which an amount of the inorganic particles is 5 wt % to 60 wt % based on a total amount of the epoxy composition, may be provided.

According to the forty-eighth embodiment of the present invention, the epoxy composition of the forty-third embodiment, in which an amount of the inorganic particles is 1 wt % to 75 wt % based on a total amount of a resin, may be provided.

According to the forty-ninth embodiment of the present invention, the epoxy composition of the forty-second embodiment, in which the fiber is at least one selected from the group consisting of a glass fiber selected from the group consisting of an E glass fiber, a T glass fiber, an S glass fiber, an NE glass fiber, an E glass fiber, a D glass fiber and a quartz glass fiber, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber, may be provided.

According to the fiftieth embodiment of the present invention, the epoxy composition of the forty-ninth embodiment, in which the fiber is the E glass fiber, may be provided.

According to the fifty-first embodiment of the present invention, the epoxy composition of the forty-ninth embodiment, in which the fiber is the T glass fiber, may be provided.

According to the fifty-second embodiment of the present invention, the epoxy composition of the forty-second embodiment, the forty-ninth embodiment, the fiftieth embodiment, or the fifty-first embodiment, in which an amount of the fiber is 10 wt % to 90 wt % based on a total amount of the epoxy composition, may be provided.

According to the fifty-third embodiment of the present invention, there is provided an electronic material including the epoxy composition according to any one of the twenty-ninth embodiment to the fifty-second embodiment.

According to the fifty-fourth embodiment of the present invention, there is provided a prepreg including the epoxy composition according to any one of the twenty-ninth embodiment to the fifty-second embodiment.

According to the fifty-fifth embodiment of the present invention, there is provided a laminate including a metal layer placed on the prepreg of the fifty-fourth embodiment.

According to the fifty-sixth embodiment of the present invention, there is provided a substrate including the epoxy composition according to any one of the twenty-ninth embodiment to the fifty-second embodiment.

According to the fifty-seventh embodiment of the present invention, there is provided a film including the epoxy composition according to any one of the twenty-ninth embodiment to the fifty-second embodiment.

According to the fifty-eighth embodiment of the present invention, there is provided a printed circuit board including the prepreg according to the fifty-fourth embodiment.

According to the fifty-ninth embodiment of the present invention, there is provided a semiconductor device including the printed circuit board of the fifty-eighth embodiment.

According to the sixtieth embodiment of the present invention, there is provided a semiconductor packaging material including the epoxy composition according to any one of the twenty-ninth embodiment to the fifty-second embodiment.

According to the sixty-first embodiment of the present invention, there is provided a semiconductor device including the semiconductor packaging material of the sixtieth embodiment.

According to the sixty-second embodiment of the present invention, there is provided an adhesive including the epoxy composition according to any one of the twenty-ninth embodiment to the fifty-second embodiment.

According to the sixty-third embodiment of the present invention, there is provided a paint composition including the epoxy composition according to any one of the twenty-ninth embodiment to the fifty-second embodiment.

According to the sixty-fourth embodiment of the present invention, there is provided a composite material including the epoxy composition according to any one of the twenty-ninth embodiment to the fifty-second embodiment.

According to the sixty-fifth embodiment of the present invention, there is provided a cured product formed of the epoxy composition according to any one of the twenty-ninth embodiment to the fifty-second embodiment.

According to the sixty-sixth embodiment of the present invention, there is provided a cured product formed of the epoxy composition according to any one of the thirty-fifth embodiment to the fifty-second embodiment, having a coefficient of thermal expansion of 15 ppm/° C. or less.

According to the sixty-seventh embodiment of the present invention, there is provided a cured product formed by using the epoxy composition according to any one of the thirty-fifth embodiment to the fifty-second embodiment, having a glass transition temperature of 100° C. or over, or not exhibiting the glass transition temperature.

According to the sixty-eighth embodiment of the present invention, there is provided a cured product formed by using the epoxy composition according to any one of the twenty-ninth embodiment to the thirty-fourth embodiment, having a coefficient of thermal expansion of 50 ppm/° C. to 150 ppm/° C.

Advantageous Effects

Chemical bonding efficiency between an epoxy compound and a filler compound may be increased due to the chemical bonding of an alkoxysilyl group in the epoxy compound and the filler in the composite of the novel epoxy composition including an epoxy compound having an alkoxysilyl group according to the present invention. Due to the increase in chemical bonding efficiency, heat-resistant properties may be improved. That is, the CTE of the epoxy composite may be decreased, and the glass transition temperature may be increased or a glass transition temperature may not be present (hereinafter, 'Tg-less'). In addition, a cured product including the epoxy compound having the alkoxysilyl group in accordance with the present invention may show good flame retardant properties through the introduction of the alkoxysilyl group.

Further, when the epoxy composition is applied to a metal film of a substrate, good adhesive properties may be exhibited with respect to the metal film due to the chemical bonding between the functional groups at the surface of the metal film and the alkoxysilyl group. In addition, due to the increase in chemical bonding efficiency of the composition including the alkoxysilylated isocyanurate epoxy compound, a silane coupling agent used in common epoxy compositions may not necessarily be included in the composition including the alkoxysilylated isocyanurate epoxy compound. The epoxy composition including the epoxy compound may have good curing efficiency, and a composite formed through the curing thereof may show good thermal expansion properties such as a low CTE and a high glass transition temperature or Tg-less.

DESCRIPTION OF DRAWINGS

The above and other embodiments, features and other advantages of the present invention will be more clearly understood from the following detailed description taken in conjunction with the accompanying drawings, in which.

BEST MODE

Figure 1:
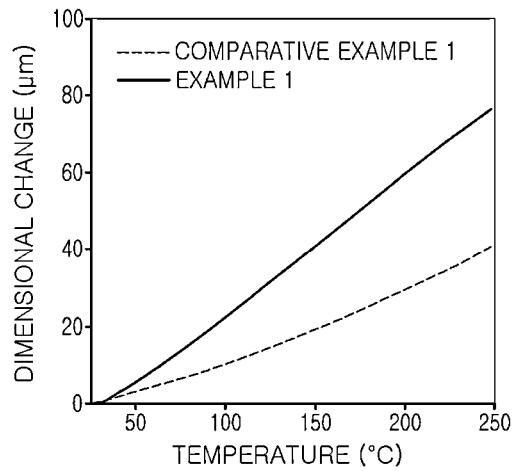
FIG. 1 is a graph illustrating dimensional changes with respect to the change of a temperature according to the composites of Example 1 and Comparative Example 1.

Exemplary embodiments of the present invention will now be described in detail with reference to the accompanying drawings.

The present invention provides a new alkoxysilylated isocyanurate epoxy compound of which a cured composite exhibits improved heat resistance properties, particularly a low CTE and a high Tg or Tg-less and/or of which a cured product exhibits good flame retardant properties, a method of preparing the same, an epoxy composition including the same, a cured product formed by using the composition and a use of the composition. In the present invention, "composite" refers to a cured product formed by using a composition including an epoxy compound and an inorganic material (fiber and/or inorganic particles). In the present invention, "cured product" refers to a cured product formed by using a composition including an epoxy compound, for example, a cured product formed by using a composition including an epoxy compound; a curing agent; and at least one selected from the group consisting of an optional inorganic material (filler), an optional curing accelerator and other additives. In addition, the term "cured product" is also used to denote a "partially-cured product".

When forming a composite through curing the epoxy composition including the alkoxysilylated isocyanurate compound in accordance with the present invention, the epoxy group may react with a curing agent to conduct a curing reaction, and the alkoxysilyl group may form an interface bond with the surface of the filler, an inorganic material. Thus, very high chemical bonding efficiency in an epoxy composite system may be obtained, and thus, a low CTE and high glass transition temperature increasing effect or Tg-less may be achieved. Therefore, dimensional stability may be improved. In addition, any additional silane coupling agent is not necessary. Further, the cured product including the alkoxysilylated isocyanurate epoxy compound according to the present invention may exhibit good flame retardant properties.

Further, the epoxy composition including the alkoxysilylated isocyanurate epoxy compound according to the present invention may exhibit good curing properties.

In addition, when applying the epoxy composition of the present invention on a chemically-treated metal film such as a copper film, a chemical bond may be formed with a —OH group or the like at the surface of the metal produced through the metal surface treatment, in order to show good adhesion with the metal film.

1. Compounds

In accordance with one embodiment of the present invention, an isocyanurate epoxy compound having an alkoxysilyl group having a structure illustrated by Formula 1 is provided.

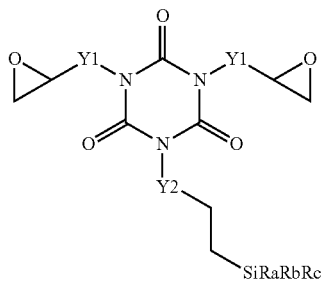

[Formula 1]

In the above Formula 1, Y1 and Y2 are independently selected from the group consisting of a C1-C10 alkanediyl, for example, a C2-C10 alkanediyl, for example, a C1-C4 alkanediyl, for example, a C2-C4 alkanediyl, for example, a C9-C10 alkanediyl, a C6-C10 aryldiyl and a C7-C10 arylated alkanediyl group and may be the same or different. The alkanediyl group may be linear or branched and cyclic or acyclic, and the alkanediyl, the aryldiyl and the arylated alkanediyl group may or may not include a heteroatom of N, O, S or P.

In the above Formula 1, Y1 is selected from the group consisting of for example, a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl, the aryldiyl and the arylated alkanediyl group may or may not include a heteroatom of N, O, S or P.

In the above Formula 1, Y2 is selected from the group consisting of for example, a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl group, the aryldiyl group and the arylated alkanediyl group may or may not include a heteroatom of N, O, S or P.

In another embodiment of the present invention, an isocyanurate epoxy compound having an alkoxysilyl group of the above Formula 1, in which Y1 is selected from the group consisting of a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group, and Y2 is selected from the group consisting of a C2-C10 alkanediyl, for example, a C9-C10 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl group, the aryldiyl group and the arylated alkanediyl group may or may not include a heteroatom of N, O, S or P, is provided.

In further another embodiment of the present invention, an isocyanurate epoxy compound having an alkoxysilyl group of the above Formula 1, in which Y1 is selected from the group consisting of a C2-C10 alkanediyl, for example, a C2-C4 alkanediyl, a C6-C10 aryldiyl and a C7-C10 arylated alkanediyl group, and Y2 is selected from the group consisting of a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl group, the aryldiyl group and the arylated alkanediyl group may or may not include a heteroatom of N, O, S or P, is provided.

In addition, in further another embodiment of the present invention, an isocyanurate epoxy compound having an alkoxysilyl group of the above Formula 1, in which Y1 is selected from the group consisting of a C2-C10 alkanediyl, for example, a C2-C4 alkanediyl, a C6-C10 aryldiyl and a C7-C10 arylated alkanediyl group, and Y2 is selected from the group consisting of a C2-C10 alkanediyl, for example, a C9-C10 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl, the aryldiyl and the arylated alkanediyl group may or may not include a heteroatom of N, O, S or P, is provided.

At least one of $R_a$ to $R_c$ is a C1-C10 alkoxy group, and the remainders thereof are a C1-C10 alkyl group, a C6-C10 aryl group, or a C7-C10 aralkyl (arylated alkyl) group. The alkyl group and the alkoxy group may be linear or branched and cyclic or acyclic, and the alkyl, the alkoxy, the aryl and the aralkyl group may or may not include a heteroatom of N, O, S or P. For example, $R_a$ to $R_c$ may be an ethoxy group.

Some definitions on Y1, Y2, and $R_a$ to $R_c$ may be applied to a method of preparing an alkoxysilylated isocyanurate epoxy compound and a composition including the same explained hereinafter.

The term "alkoxy" used in the present application refers to a monovalent —OR (R is an alkyl) group, may be linear or branched, may be cyclic or acyclic, and may or may not include a heteroatom of N, O, S or P.

The term "alkyl" used in the present application refers to a monovalent hydrocarbon group, may be linear or branched, may be cyclic or acyclic, and may or may not include a heteroatom of N, O, S or P.

The term "alkanediyl" used in the present application refers to a divalent hydrocarbon group, may be linear or branched, may be cyclic or acyclic, and may or may not include a heteroatom of N, O, S or P.

The term "aryl" used in the present application refers to a monovalent aromatic hydrocarbon group, and may or may not include a heteroatom of N, O, S or P.

The term "aryldiyl" used in the present application refers to a divalent aromatic hydrocarbon group, and may or may not include a heteroatom of N, O, S or P.

The term "aralkyl", that is, an arylated alkyl used in the present application refers to a monovalent group in which one hydrogen atom of the alkyl group is substituted with an aryl group and may or may not include a heteroatom of N, O, S or P.

The term "arylated alkanediyl" used in the present application refers to a divalent group, in which one hydrogen atom of the alkyl group is substituted with an aryl group, and may or may not include a heteroatom of N, O, S or P.

The isocyanurate epoxy compound having an alkoxysilyl group according to an embodiment of the present invention may have, for example, the following Formulae (A) to (C).

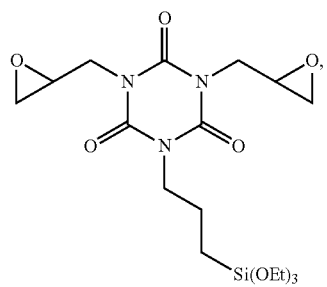

(A)

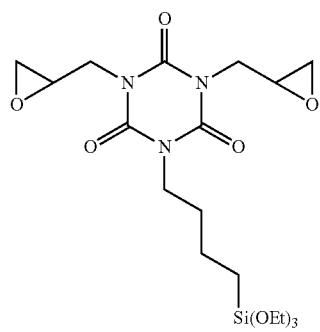

(B)

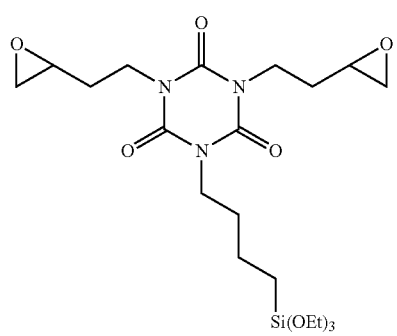

(C)

According to an embodiment of the present invention, there is provided a reaction intermediate having a structure illustrated by Formulae (D) to (F).

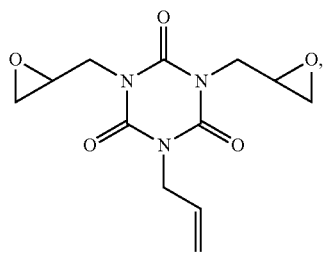

(D)

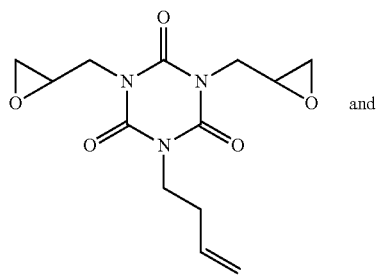

(E)

and

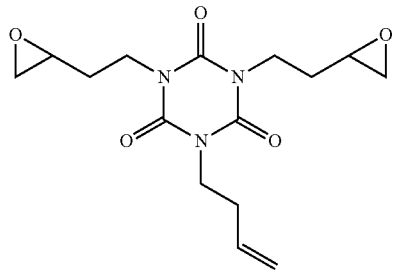

(F)

According to further another embodiment of the present invention, there is provided an epoxy polymer having a structure illustrated by Formula 2.

[Formula 2]

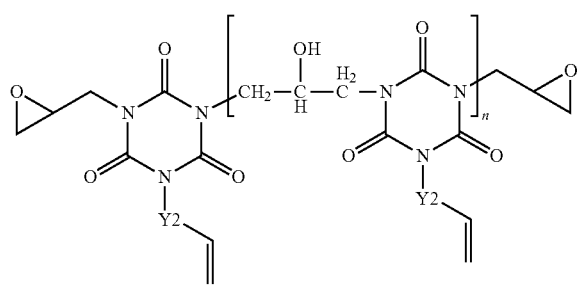

In the above Formula 2, Y2 is the same as that defined in Formula 1 according to an embodiment; n means an integer of 0 to 100, and preferably, an integer of 0 to 10. The epoxy polymer of the above Formula 2 may be prepared by the reaction of a nitrogen atom of a starting material having a structure illustrated by Formula 2-1 with an epoxy group of the reaction intermediate of Formula 3 during preparing the alkoxysilylated isocyanurate epoxy compound according to an embodiment of the present invention according to method 1 to be explained hereinafter. The term "epoxy polymer" in the present application includes an oligomer and a polymer.

2. Method of Preparing Epoxy Compounds

In accordance with other exemplary embodiments of the present invention, a method of preparing an isocyanurate epoxy compound having an alkoxysilyl group of the above Formula 1 is provided. The isocyanurate epoxy compound having an alkoxysilyl group of the above Formula 1 may be prepared by the following two methods. Each method will be explained in detail.

(Method 1)

According to an embodiment of the present invention, an isocyanurate epoxy compound having an alkoxysilyl group of the above Formula 1 (Y1=—CH$_2$—) may be prepared by a method including an epoxidation and an alkenylation of a starting material (first step) and an alkoxysilylation (second step). Hereinafter, this method is referred to as method 1 and will be explained.

In the first step, a diglycidyl isocyanurate intermediate having a structure illustrated by Formula 3 (Y1=—CH$_2$—) is prepared by the reaction of isocyanuric acid (1,3,5-triazinane-2,4,6-trione) having a structure illustrated by Formula 2-1, epichlorohydrin, and an alkenyl compound having a structure illustrated by Formula R1. Particularly, the reaction intermediate of Formula 3 is prepared by the alkenylation of an amine of the starting material having a structure illustrated by Formula 2-1 and a subsequent in situ epoxidation reaction (method 1), or the reaction intermediate of Formula 3 is prepared by the epoxidation of the amine of the starting material having a structure illustrated by Formula 2-1 and a subsequent in situ alkenylation reaction (method 2) in the first step. In the second step, an alkoxysilylated isocyanurate epoxy compound of the above Formula 1 of which Y1 is —CH$_2$—, according to an embodiment of the present invention is prepared by the reaction of the reaction intermediate having a structure illustrated by Formula 3 and an alkoxysilane.

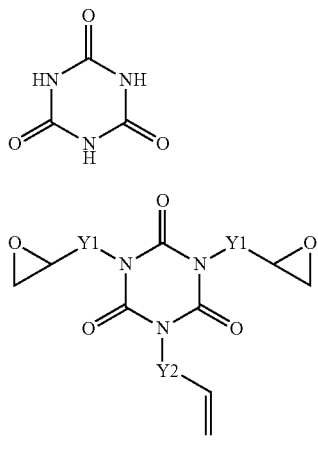

[Formula 2-1]

[Formula 3]

[Formula R1]

In the above Formula 3, Y is —CH$_2$—, and in Formulae 3 and R1, Y2 is selected from the group consisting of a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl, the aryldiyl and the arylated alkanediyl group may or may not include a heteroatom of N, O, S or P.

In the above Formula R1, X is Cl, Br, I, —O—SO$_2$—CH$_3$, —O—SO$_2$CF$_3$, or —O—SO$_2$—C$_6$H$_4$—CH$_3$.

Since the amine group of the isocyanuric acid of the above Formula 2-1, the epichlorohydrin and the alkenyl compound react by the equivalent ratio according to stoichiometry, the alkenyl compound of the above Formula R1 is added so that an alkenyl group is 0.3 to 5 equivalents with respect to 1 equivalent of the amine of the compound of Formula 2-1, and then, the epichlorohydrin is subsequently added so that the epichlorohydrin is 1 to 10 equivalents with respect to 1 equivalent of the amine of the isocyanuric acid of the above Formula 2-1, and a reaction is conducted in situ (hereinafter will be referred to as 'method 1').

As described above, the reaction in the first step may be conducted by reacting the isocyanuric acid starting material of Formula 2-1 with epichlorohydrin first and then, the alkenyl compound is subsequently added in situ to initiate the reaction with a compound for alkenylation (hereinafter will be referred to as 'method 2'). However, the control of the concentration of the alkenyl group and/or the epoxy group and the molecular weight is easier in method 1 as compared to method 2. When the reaction of the first step is conducted according to method 2, the equivalent ratio of the starting material and the alkylene compound and reaction conditions may be the same as those in method 1, and the same reaction conditions may be applied in the reaction with the epichlorohydrin except for using 0.6 to 10 equivalents of the epichlorohydrin with respect to 1 equivalent of an amine. That is, the reaction of 0.6 to 10 equivalents of the epichlorohydrin with respect to 1 equivalent of the amine of the compound of Formula 2-1 is conducted, and then, the reaction of 0.3 to 5 equivalents of the alkenyl group of the alkenyl compound of the above Formula R1 with respect to 1 equivalent of the amine of the above Formula 2-1 is subsequently conducted in situ.

The equivalent ratio of the reaction material in the reaction may be easily controlled by a person skilled in the art by the number of functional groups (for example, alkenyl group and/or epoxy group) within the range of the equivalent ratio, and the same way may be applied in other methods and each reaction step in each method described hereinafter.

In the first step, the epoxidation reaction is performed at room temperature (for example, 15° C. to 25° C.) to 150° C. for 1 to 24 hours, and the alkenylation reaction is performed after adding the alkenyl compound of the above Formula R1 at room temperature (for example, 15° C. to 25° C.) to 150° C. for 1 to 24 hours.

The reaction temperature and the reaction time of the epoxidation reaction in the first step may change according to the kind of the base, and the reaction may be performed, for example, at room temperature (for example, 15° C. to 25° C.) to 150° C. for 1 to 24 hours. The reaction temperature and the reaction time of the alkenylation reaction may change according to the kind of the alkenyl compound, and the reaction may be performed, for example, at room temperature (for example, 15° C. to 25° C.) to 150° C. for 1 to 24 hours, and an epoxy compound, a reaction intermediate of Formula 3 may be obtained.

The reaction in the first step, particularly, the alkenylation reaction and the epoxidation reaction are respectively conducted in the presence of a base, an optional catalyst and an optional solvent, respectively. Particularly, the base is added during the alkenylation reaction and the epoxidation reaction, separately. The optional catalyst may be added during the first reaction among the alkenylation reaction and the epoxidation reaction irrespective of the reaction order. The optional solvent may be added during the first reaction irrespective of the reaction order, or may be appropriately added during both of the two reactions.

As the base in the alkenylation and the epoxidation reactions in the first step, a strong base such as NaH, KOH or NaOH may be used, and a weak base such as $K_2CO_3$ and $Na_2CO_3$ may be used without limitation. These bases may be used alone or two or more bases may be used together. In each of the alkenylation and the epoxidation reactions, 0.3 to 5 equivalents of the base with respect to 1 equivalent of the aromatic amine of the compound of Formula 2-1 is preferably used in consideration of reaction efficiency. The base is added for the de-protonation of a proton from nitrogen in the compound of Formula 2-1. The base is added during the alkenylation reaction and the epoxidation reaction separately.

In the reaction of the first step, the catalyst may be optionally used as occasion demands and may include a phase transition catalyst, for example, tetramethylammonium chloride, tetramethylammonium bromide, tetrabutylammonium iodide, trimethylbenzylammonium chloride, and triethylbenzylammonium chloride without limitation. These compounds may be used alone or two or more compounds may be used together. 0.01 to 0.05 equivalents of the catalyst with respect to 1 equivalent of the aromatic amine of the compound of Formula 2-1 is preferably used in consideration of reaction efficiency.

The solvents may be optionally used as occasion demands in the first step reaction. For example, when the viscosity of the reactants at a reaction temperature is appropriate for conducting the reaction without a separate solvent in the first step reaction, the solvent may not be necessary. That is, when the viscosity of the reactants is sufficiently low that the mixing and the stirring of the reactants may be conducted smoothly without a solvent, separate use of the solvent may not be necessary. This state may be easily understood by a person skilled in the art. When the solvent is used, any organic solvents that may easily dissolve the reactants, that do not have any adverse effects, and that may be easily removed after the reaction, may be used without limitation. For example, 1,4-dioxane, acetonitrile, tetrahydrofuran (THF), dimethylformamide (DMF), dimethyl sulfoxide (DMSO), methanol, ethanol, or the like, may be used. These solvents may be used alone or as a mixture of two or more thereof. The amount of the solvent may not be limited to a specific range, and an appropriate amount of the solvent may be used within a range for sufficiently dissolving the reactants and not adversely affecting the reaction. A person skilled in the art may select an appropriate amount of the solvent in consideration of the above-mentioned points.

As described above, a polymer of the above Formula 2 may be formed through the reaction of the nitrogen atom of the starting material having a structure illustrated by Formula 2-1 and the epoxy group of the reaction intermediate of Formula 3 during performing the first step reaction.

Subsequently, through the reaction of alkoxysilane with the reaction intermediate of the above Formula 3 obtained in the first step, the alkenyl group of Formula 3 is alkoxysilylated, and an isocyanurate epoxy compound having an alkoxysilyl group of Formula 1 according to an embodiment of the present invention is obtained.

In the second step, the reaction intermediate of the above Formula 3 and the alkoxysilane having a structure illustrated by Formula R2 react so that 1 to 3 equivalents of the alkoxysilane having a structure illustrated by Formula R2 and 1 equivalent of the alkenyl group of the reaction intermediate of the above Formula 3 may react. In addition, the second step is conducted in the presence of a metal catalyst and an optional solvent. Further, the second step reaction may be conducted at room temperature (for example, 15° C. to 25° C.) to 120° C. for 1 to 72 hours.

$$HSiR_aR_bR_c \qquad \text{[Formula R2]}$$

In the above Formula R2, at least one of $R_a$ to $R_c$ is a C1-C10 alkoxy group, and the remainders thereof are a C1-C10 alkyl group, a C6-C10 aryl group, or a C7-C10 aralkyl group, the alkoxy group and the alkyl group may be linear or branched and cyclic or acyclic, and the alkoxy, the alkyl, the aryl and the aralkyl group may or may not include a heteroatom of N, O, S or P. Preferably, $R_a$ to $R_c$ may be an ethoxy group.

In the second step reaction, since the reaction intermediate of Formula 3 and the alkoxysilane react so that the alkenyl group of the reaction intermediate and the alkoxysilane react by the equivalent ratio according to stoichiometry, the reaction intermediate of Formula 3 and the alkoxysilane react so that 1 to 3 equivalents of the alkoxysilane of the above Formula R2 and 1 equivalent of the alkenyl substituent of the above Formula 3 may react.

The reaction temperature and the reaction time in the second step reaction may change according to the kinds of the reactants, and a reaction may be conducted, for example, at room temperature (for example, 15° C. to 25° C.) to 120° C. for 1 to 72 hours to obtain an isocyanurate epoxy compound having an alkoxysilyl group of the above Formula 1.

In the second step reaction, the metal catalyst may include, for example, $PtO_2$ or $H_2PtCl_6$ (chloroplatinic acid) without limitation. 0.01 to 0.05 equivalents of a platinum catalyst with respect to 1 equivalent of the alkenyl group of Formula 3 may be preferably used in consideration of reaction efficiency.

The solvents may be optionally used as occasion demands in the second step reaction. For example, when the viscosity of the reactants at a reaction temperature is appropriate for conducting the reaction without a separate solvent in the second step reaction, the solvent may not be necessary. That is, when the viscosity of the reactants is sufficiently low that the mixing and the stirring of the reactants may be conducted smoothly without the solvent, the separate use of a solvent may not be necessary. This state may be easily understood by a person skilled in the art. When the solvent is used, any aprotic solvents that may easily dissolve the reactants, that do not have any adverse effects, and that may be easily removed after the reaction, may be used without limitation. For example, toluene, acetonitrile, THF, MEK, DMF, DMSO, methylene chloride (MC), or the like, may be used. These solvents may be used alone or as a mixture of two or more thereof. The amount of the solvent may not be limited to a specific range, and an appropriate amount of the solvent may be used within a range for sufficiently dissolving the reactants and not adversely affecting the reaction. A person skilled in the art may select an appropriate amount of a solvent considering the above-mentioned points.

An isocyanurate epoxy compound having an alkoxysilyl group of the above Formula 1 (in this case, Y1 is —$CH_2$— in Formula 1) is obtained through the first and second steps of method 1. Since the starting material of Formula 2-1 reacts with epichlorohydrin in the above method 1, an epoxy compound of Formula 1 in which Y1 is —$CH_2$— is obtained. Y2 may be any Y2 groups defined in Formula 1 according to Formula R1 used.

The reaction scheme of method 1 is as follows.

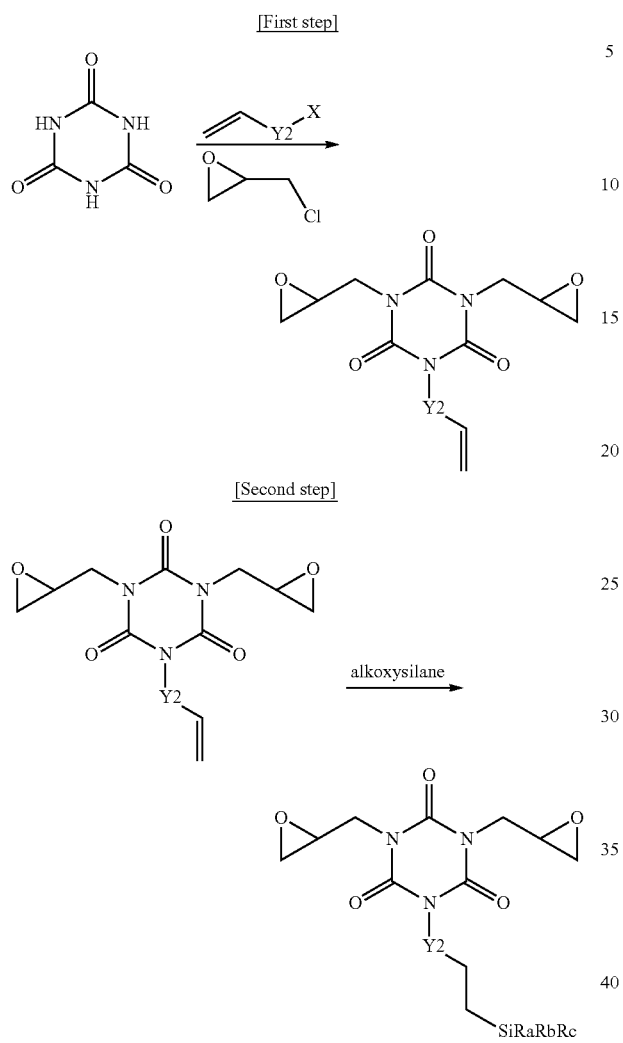

(In the reaction scheme, Y2 and Ra, Rb and Rc are the same as defined above.)

(Method 2)

According to another embodiment of the present invention, an isocyanurate epoxy compound having an alkoxysilyl group of the above Formula 1 is prepared by a method including an epoxidation of the starting material having a structure illustrated by Formula 2-2 (first step) and an alkoxysilylation (second step). Hereinafter, this method will be referred to as 'method 2' and will be described in detail.

Particularly, the reaction intermediate having a structure illustrated by Formula 3 is obtained by the reaction of the trialkenyl isocyanurate starting material having a structure illustrated by Formula 2-2 and a peroxide compound in the first step. That is, the reaction intermediate having a structure illustrated by Formula 3 is obtained through the epoxidation of two alkenyl groups among the three alkenyl groups of the starting material of Formula 2-2 by the peroxide compound. As described above, the number of the alkenyl groups to be epoxidized may be controlled by controlling the equivalent ratio of the reactants, and the control thereof may be easily conducted by a person skilled in the art.

[Formula 2-2]

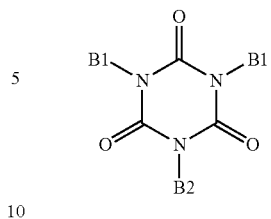

In the above Formula 2-2, B1 is —Y1-CH=CH$_2$, and B2 is —Y2-CH=CH2.

[Formula 3]

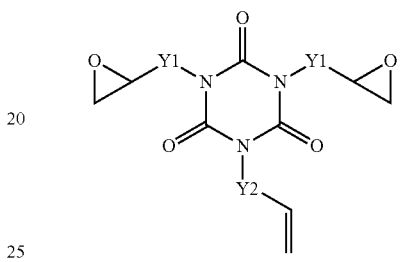

Y1 in B1 and Y2 in B2, and Y1 and Y2 in the above Formula 3 are the same as those defined in the alkoxysilylated isocyanurate epoxy compound of the above Formula 1 provided in any embodiment of the present invention.

Particularly, Y1 and Y2 may be independently selected from the group consisting of a C1-C10 alkanediyl, for example, a C2-C10 alkanediyl, for example, a C1-C4 alkanediyl, for example, a C2-C4 alkanediyl, for example, a C9-C10 alkanediyl, a C6-C10 aryldiyl and a C7-C10 arylated alkanediyl group and may be the same or different.

In addition, Y1 may be selected from the group consisting of a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group. Y2 may be selected from the group consisting of, for example, a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group.

In an embodiment, Y1 may be selected from the group consisting of a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group, and Y2 may be selected from the group consisting of a C2-C10 alkanediyl, for example, a C2-C4 alkanediyl, a C6-C10 aryldiyl and a C7-C10 arylated alkanediyl group. In another embodiment, Y1 may be selected from the group consisting of a C2-C10 alkanediyl, for example, a C2-C4 alkanediyl, a C6-C10 aryldiyl and a C7-C10 arylated alkanediyl group, and Y2 may be selected from the group consisting of a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. In further another embodiment, Y1 may be selected from the group consisting of a C2-C10 alkanediyl, for example, a C2-C4 alkanediyl, a C6-C10 aryldiyl and a C7-C10 arylated alkanediyl group, and Y2 may be selected from the group consisting of a C2-C10 alkanediyl, for example, a C9-C10 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl, the aryldiyl and the arylated alkanediyl group may have a heteroatom of N, O, S, or P, or not.

In the first step, since the alkenyl group of the compound of the above Formula 2-2 and the peroxide compound react by the equivalent ratio according to stoichiometry, the compound of the above Formula 2-2 and the peroxide compound react so that 1 to 5 equivalents of the peroxide group of the peroxide compound with respect to 1 equivalent of the alkenyl group of Formula 2-2 may react. Further, the first step reaction may be conducted in the presence of an optional base and an optional solvent. In addition, the first step reaction may be conducted at room temperature (for example, 15° C. to 25° C.) to 100° C. for 1 to 120 hours.

The reaction temperature and the reaction time of the first step may change according to the structure of Formula 2-2 and according to the kind of the trialkenyl isocyanurate compound, and the reaction may be performed, for example, at room temperature (for example, 15° C. to 25° C.) to 100° C. for 1 to 120 hours to obtain the reaction intermediate of Formula 3.

The peroxide compound may include meta-chloroperoxybenzoic acid (m-CPBA), $H_2O_2$, dimethyldioxirane (DMDO), and oxone without limitation. These peroxide compounds may be used alone or as a mixture of two or more thereof.

In the first step reaction, the base may be optionally used as occasion demands. The base is used to neutralize an acid component possibly remain according to the kind of the peroxide compound used after the reaction. The examples of the base used may include, KOH, NaOH, $K_2CO_3$, $KHCO_3$, NaH, triethylamine, and diisopropylethyl amine without limitation. These bases may be used alone or as a mixture of two or more thereof. In the case when the base is used, 1 to 5 equivalents of the base with respect to 1 equivalent of the alkenyl group of the compound of Formula 2-2 is preferably used in consideration of reaction efficiency.

The solvents may be optionally used as occasion demands in the first step reaction. For example, when the viscosity of the reactants at the reaction temperature is appropriate for conducting the reaction without a separate solvent in the first step reaction, the solvent may not be necessary. That is, when the viscosity of the reactants is sufficiently low that the mixing and the stirring of the reactants may be conducted smoothly without the solvent, the separate use of a solvent may not be necessary. This state may be easily understood by a person skilled in the art. When the solvent is used, any organic solvents that may easily dissolve the reactants, that do not have any adverse effects, and that may be easily removed after the reaction, may be used without limitation. For example, acetonitrile, THF, MEK, DMF, MC, DMSO, chloroform, or the like, may be used. These solvents may be used alone or as a mixture of two or more thereof. The amount of the solvent may not be limited to a specific range, and an appropriate amount of the solvent may be used within a range for sufficiently dissolving the reactants and not adversely affecting the reaction. A person skilled in the art may select an appropriate amount of a solvent in consideration of the above-mentioned points.

The second step in method 2 is the same as the second step in method 1. Particularly, all reaction conditions including the reaction temperature, the reaction time, the equivalent ratio of reactants, the metal catalyst and the kind and amount used of the optional solvent are the same as those in the second step in method 1.

The reaction scheme of the above method 2 is as follows.

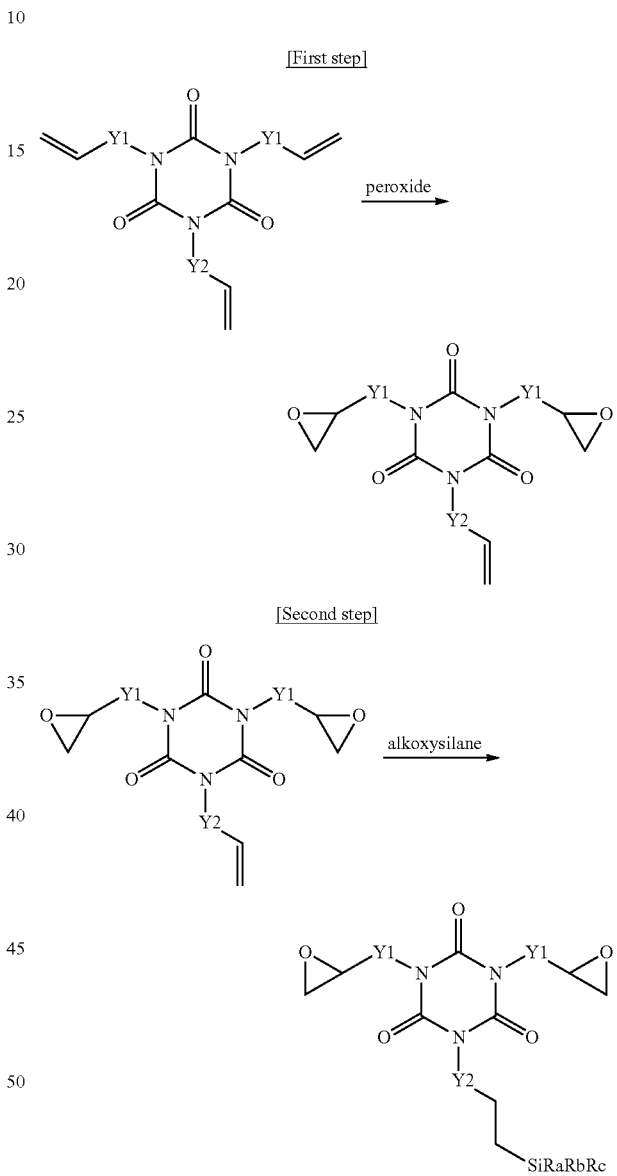

In the above reaction, Y1 and Y2 are the same as those defined in the above Formula 2-2, and $R_a$, $R_b$ and $R_c$ are the same as defined in the above Formula 1.

Meanwhile, the compound of the above Formula 2-2 used as the starting material in method 2 may be purchased from commercial products, or may be prepared by alkenylating the starting material of Formula 2-1 of method 1.

Particularly, the compound of the above Formula 2-2 may be obtained through the reaction of the isocyanuric acid of the above Formula 2-1 with the alkenyl compound having a structure illustrated by Formula R1.

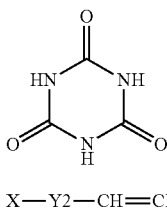

X—Y2—CH=CH$_2$  [Formula R1]

In the above Formula R1, Y2 is the same as that defined in the above Formulae 2-2 and 3, and X is Cl, Br, I, —O—SO$_2$—CH$_3$, —O—SO$_2$—CF$_3$, or —O—SO$_2$—C$_6$H$_4$—CH$_3$.

Since the amine group of the isocyanuric acid of the above Formula 2-1 and the alkenyl compound of the above Formula R1 react by the equivalent ratio according to stoichiometry, the reaction may be conducted by adding 1 to 5 equivalents of the alkenyl group of the alkenyl compound of the above Formula R1 with respect to 1 equivalent of the amine of the compound of Formula 2-1 in consideration of the equivalent ratio.

The alkenylation reaction is conducted in the presence of a base, an optional catalyst and an optional solvent. The reaction temperature and the reaction time of the alkenylation reaction change according to the kind of the alkenyl group, and the compound of the above Formula 2-2 is obtained through the reaction, for example, at room temperature (for example, 15° C. to 25° C.) to 150° C. for 1 to 24 hours.

As the base, a strong base such as NaH, KOH or NaOH may be used, and a weak base such as K$_2$CO$_3$ and Na$_2$CO$_3$ may be used, without limitation, according to conditions. These bases may be used alone or two or more bases may be used together. 0.3 to 5 equivalents of the base with respect to 1 equivalent of the aromatic amine of the compound of Formula 2-1 is preferably used in consideration of reaction efficiency. The base is added for the de-protonation of a proton from nitrogen in the compound of Formula 2-1.

In the reaction of the first step, the catalyst may be optionally used as occasion demands and may include a phase transition catalyst, for example, tetramethylammonium chloride, tetramethylammonium bromide, tetrabutylammonium iodide, trimethylbenzylammonium chloride, and triethylbenzylammonium chloride without limitation. These compounds may be used alone or two or more compounds may be used together. 0.01 to 0.05 equivalents of the catalyst with respect to 1 equivalent of the aromatic amine of the compound of Formula 2-1 is preferably used in consideration of reaction efficiency.

The solvents may be optionally used as occasion demands in the first step reaction. For example, when the viscosity of the reactants at the reaction temperature is appropriate for conducting the reaction without a separate solvent in the first step reaction, the solvent may not be necessary. That is, when the viscosity of the reactants is sufficiently low that the mixing and the stirring of the reactants may be conducted smoothly without the solvent, the separate use of a solvent may not be necessary. This state may be easily understood by a person skilled in the art. When the solvent is used, any organic solvents that may easily dissolve the reactants, that do not have any adverse effects, and that may be easily removed after the reaction, may be used without limitation. For example, 1,4-dioxane, acetonitrile, THF, DMF, DMSO, methanol, ethanol, or the like, may be used. These solvents may be used alone or as a mixture of two or more thereof. The amount of the solvent may not be limited to a specific range, and an appropriate amount of the solvent may be used within a range for sufficiently dissolving the reactants and not adversely affecting the reaction. A person skilled in the art may select an appropriate amount of a solvent in consideration of the above-mentioned points.

The alkenylation reaction is as follows.

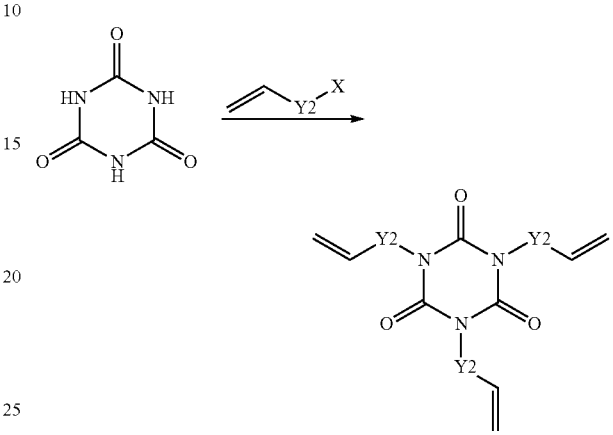

As described above, when preparing the starting material of Formula 2-2, B1 and B2, which are the alkenyl parts of the above Formula 2-1 are derived from the alkenyl compound of the above Formula R1, and B1 and B2 in Formula 2-2 are the same (that is, Y1 and Y2 are the same). Therefore, B1 and B2 are represented by Y2 for convenience in the above reaction, and Y2 is the same as that defined in the above Formulae 2-2 and 3.

3. Epoxy Composition

According to another embodiment of the present invention, a composition including the alkoxysilylated isocyanurate epoxy compound of Formula 1 according to an embodiment of the present invention is provided. Particularly, in the above Formula 1, Y1 and Y2 are selected from the group consisting of a C1-C10 alkanediyl, for example, a C2-C10 alkanediyl, for example, a C1-C4 alkanediyl, for example, a C2-C4 alkanediyl, for example, a C9-C10 alkanediyl, a C6-C10 aryldiyl and a C7-C10 arylated alkanediyl group, and may be the same or different.

In an embodiment, Y1 may be selected from the group consisting of a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group. In an embodiment, Y2 may be selected from the group consisting of, for example, a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. In addition, in an embodiment, Y1 may be selected from the group consisting of a C1-C10 alkanediyl, for example, a C2-C10 alkanediyl, for example, a C1-C4 alkanediyl, for example, a C2-C4 alkanediyl, a C6-C10 aryldiyl and a C7-C10 arylated alkanediyl group, and Y2 may be selected from the group consisting of a C2-C10 alkanediyl, for example, a C9-C10 alkanediyl, for example, a C2-C4 alkanediyl, a C6-C10 aryldiyl and a C7-C10 arylated alkanediyl group. In further another embodiment, Y1 may be selected from the group consisting of a C2-C10 alkanediyl, for example, a C2-C4 alkanediyl, a C6-C10 aryldiyl and a C7-C10 arylated alkanediyl group, and Y2 may be selected from the group consisting of a C1-C10 alkanediyl, for example, a C2-C10 alkanediyl, for example, a C9-C10 alkanediyl, for example, a C1-C4 alkanediyl, for example, a C2-C4 alkanediyl, a C6-C10 aryldiyl and a C7-C10 arylated alkanediyl group. In further another embodiment, Y1 may be selected from the group consisting of a C2-C10 alkanediyl, for example, a C2-C4 alkanediyl, a C6-C10 aryldiyl and a C7-C10 arylated alkanediyl group, and Y2 may be selected from the group consisting of a C2-C10 alkanediyl, for example, a C9-C10 alkanediyl, for example, a C2-C4 alkanediyl, a C6-C10 aryldiyl and a C7-C10 arylated alkanediyl group. The alkanediyl group may be linear or branched and cyclic or acyclic, and the alkanediyl group, the aryldiyl group and the arylated alkanediyl group may have a heteroatom of N, O, S, or P, or not. In Formula 1, at least one of $R_a$ to $R_c$ may be a C1-C10 alkoxy group, and the remaining thereof may be a C1-C10 alkyl group, a C6-C10 aryl group or a C7-C10 aralkyl group, and the alkoxy group and the alkyl group may be linear or branched and cyclic or acyclic. The alkoxy, the alkyl, the aryl and the aralkyl group may or may not include a heteroatom of N, O, S, or P. Preferably, $R_a$ to $R_c$ may be an ethoxy group. The above definition may be applied to any epoxy compositions described hereinafter.

Any composition provided in the present invention may be used as an electronic material, particularly, an electronic part such as a semiconductor (for example, a substrate, an encapsulating material, a build-up film, or the like) or a printed circuit board, an adhesive, a paint composition, a composite material, or the like. In addition, any compositions provided in the present invention may be a curable composition including a curable composition and/or an inorganic material.

The epoxy composition in accordance with an example embodiment of the present invention may include any epoxy compositions of any kinds and/or in any mixing ratios commonly known in this technical field only when including any alkoxysilylated isocyanurate epoxy compounds provided by any embodiments of the present invention (hereinafter, an 'epoxy compound of the present invention'). The kind and the mixing ratio of a curing agent, a curing accelerator (catalyst), an inorganic material (filler) (for example, inorganic particles and/or a fiber), other common epoxy compounds, and other additives composing the epoxy composition may not be limited.

Further, in this technical field, various kinds of epoxy groups are used together in the epoxy composition according to the application part and/or use of the epoxy composition, a cured material and/or a composite thereof. Accordingly, as the epoxy compound in the epoxy composition in accordance with any embodiments of the present invention, an alkoxysilylated isocyanurate epoxy compound of the above Formula 1 in any embodiments of the present invention and any epoxy compounds known in this technical field (hereinafter, a "conventional epoxy compound" or a "common epoxy compound"), may be included.

The common epoxy compound may not be limited to specific compounds, but may be any epoxy compound commonly known in this technical field, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. In addition, the common epoxy compound may include at least one of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound, having as a core structure, at least one of bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic compound and a novolak unit.

For example, the common epoxy compound may be at least one of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound, having the bisphenol A, the bisphenol F, the bisphenol S, the biphenyl, the naphthalene, or the fluorene as a core structure.

Any epoxy compositions in accordance with an embodiment of the present invention may include without limitation, based on the total amount of an epoxy compound, 1 wt % to 100 wt % of the epoxy compound according to any embodiments of the present invention and 0 wt % to 99 wt % of the common epoxy compound; for example, 10 wt % to 100 wt % of the epoxy compound of the present invention and 0 wt % to 90 wt % of the common epoxy compound; for example, 30 wt % to 100 wt % of the epoxy compound of the present invention and 0 wt % to 70 wt % of the common epoxy compound; for example, from 50 wt % to 100 wt % of the epoxy compound of the present invention and from 0 wt % to 50 wt % of the common epoxy compound; for example, from 10 wt % to below 100 wt % of the epoxy compound of the present invention and from excess of 0 wt % to 90 wt % of the common epoxy compound; for example, from 30 wt % to below 100 wt % of the epoxy compound of the present invention and from excess of 0 wt % to 70 wt % of the common epoxy compound; for example, from 50 wt % to below 100 wt % of the epoxy compound of the present invention and from excess of 0 wt % to 50 wt % of the common epoxy compound.

Further, in accordance with other exemplary embodiments of the present invention, an epoxy composition including an alkoxysilylated isocyanurate epoxy compound of the above Formula 1 provided in any embodiments of the present invention and a curing agent is provided. The epoxy composition including the alkoxysilylated isocyanurate epoxy compound of the above Formula 1 and the curing agent may include any epoxy compositions of any kinds and/or any mixing ratios commonly known in this technical field only when including the alkoxysilylated isocyanurate epoxy compound of the above Formula 1 and the curing agent. The kind and the mixing ratio of a curing accelerator (catalyst), an inorganic material (filler) (for example, inorganic particles and/or a fiber), other common epoxy compounds, and other additives composing the epoxy composition may not be limited. Any epoxy compositions including any alkoxysilylated isocyanurate epoxy compound of the above Formula 1 and a curing agent may also include any common epoxy compounds as the epoxy compound. In this case, the kind of the common epoxy compounds possibly included, and the mixing ratio of the alkoxysilylated isocyanurate epoxy compound and the common epoxy compound may be the same as those described above.

In the composition including the alkoxysilylated isocyanurate epoxy compound and the curing agent in accordance with exemplary embodiments of the present invention, any curing agents commonly known as curing agents of an epoxy compound may be used. For example, an amine-based compounds, a phenol-based compounds, an acid anhydride-based compounds may be used without limitation.

More particularly, an aliphatic amine, an alicyclic amine, an aromatic amine, other amines and a modified amine may be used as the amine-based curing agent without limitation. In addition, an amine compound including two or more primary amine groups may be used. Particular examples of the amine curing agents may include at least one aromatic amine selected from the group consisting of 4,4'-dimethyl-aniline (diamino diphenyl methane, DAM or DDM), diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP) and bis(4-amino 3-methylcyclohexyl)methane, (larominc 260), other amines such as dicyanamide (DICY), or the like, and a modified amine such as a polyamide-based compound, an epoxide-based compound, or the like.

Examples of the phenol curing agent may include, without limitation, a phenol novolak resin, a cresol novolak resin, a bisphenol A novolak resin, a xylene novolak resin, a triphenyl novolak resin, a biphenyl novolak resin, a dicyclopentadiene novolak resin, phenol p-xylene, a naphthalene-based phenol novolak resin, a triazine-based compound, or the like.

Examples of the acid anhydride-based curing agent may include, without limitation, an aliphatic anhydrides such as dodecenyl succinic anhydride (DDSA), poly azelaic poly anhydride, or the like, an alicyclic anhydrides such as hexahydrophthalic anhydride (HHPA), methyl tetrahydrophthalic anhydride (MeTHPA), methylnadic anhydride (MNA), or the like, an aromatic anhydrides such as trimellitic anhydride (TMA), pyromellitic acid dianhydride (PMDA), benzophenonetetracarboxylic dianhydride (BTDA), or the like, and a halogen-based anhydrous compound such as tetrabromophthalic anhydride (TBPA), chlorendic anhydride, or the like.

In general, the crosslinking density of an epoxy composite may be controlled by the extent of reaction of the curing agent with the epoxy group. According to the range of the target crosslinking density, the amount of the curing agent may be controlled based on the concentration of the epoxy group of an epoxy compound. For example, when an amine curing agent is used, the ratio of the epoxy equivalent/amine equivalent may be preferably controlled to 0.5 to 2.0, for example, 0.8 to 1.5 in an equivalent reaction of the amine curing agent with the epoxy group.

Though the mixing ratio of the curing agent has been explained with respect to the amine-based curing agent, a phenol-based curing agent, an acid anhydride-based curing agent and any curing agents for curing epoxy compounds not separately illustrated in this application but used for curing may be used by appropriately mixing a stoichiometric amount according to the chemical reaction of the epoxy functional group and the reactive functional group of the curing agent based on the concentration of the total epoxy group in the epoxy composition according to the desired range of the curing density. The above-described parts are commonly known in this field.

An optional curing accelerator (catalyst) may be additionally included as occasion demands to promote the curing reaction in any epoxy compositions provided in the present invention. Any curing accelerators (catalysts) commonly used for curing an epoxy composition in this art may be used without limitation, for example, an imidazole-based, a tertiary amine-based, a quaternary ammonium-based, an organic acid salt-based, Lewis acids, a phosphor compound-based curing accelerator may be used.

More particularly, for example, the imidazole-based curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine-based curing accelerator such as benzyldimethylamine (BDMA), tris dimethylaminomethyl phenol (DMP-30), and triethylenediamine; the quaternary ammonium-based curing accelerator such as tetrabutylammonium bromide, or the like; diazabicycloundecene (DBU), or an organic acid of DBU; the phosphor compound-based curing accelerator such as triphenyl phosphine, phosphoric acid ester, or the like, and a Lewis acid such as $BF_3$-monoethylamine ($BF_3$-MEA), or the like, may be illustrated without limitation. Latent curing accelerators which are formed by the microcapsulation and the formation of complex salts of accelerators may also be used. These compounds may be used alone or a mixture of two or more thereof, according to curing conditions may be used.

The mixing amount of the curing accelerator may be a commonly applied mixing amount in this art without limitation. For example, 0.1 to 10 phr (parts per hundred parts of resin, parts by weight based on 100 parts by weight of the epoxy compound), for example, 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput may be expected.

Further, any epoxy compositions provided in the present invention, for example, any epoxy compositions including the alkoxysilylated isocyanurate epoxy compound and optionally at least one selected from the group consisting of a common epoxy compound, a curing agent and a catalyst, may additionally include inorganic particles or a fiber as a filler of an inorganic material.

Any inorganic particles known to be used to decrease the coefficient of thermal expansion of a common organic resin may be used. Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxane, ladder type silsesquioxane, and cage type silsesquioxane. The inorganic particles may be used alone or as a mixture of two or more thereof.

In the case when particularly a large amount of the inorganic particles are mixed, the fused silica is preferably used. The fused silica may have any shape among a cataclastic shape and a spherical shape. However, the spherical shape is preferable to increase the mixing ratio of the fused silica and to restrain the increase of the fused viscosity of a forming material.

The inorganic particles having a particle size of 0.5 nm to several tens of μm (for example, 50 μm to 100 μm) may be used in consideration of the use of a composite, particularly, the dispersibility of the inorganic particles, or the like. Since the dispersibility of the inorganic particles dispersed in the epoxy matrix may be different according to the particle size, the inorganic particles having the above-described size may preferably be used. In addition, the distribution range of the inorganic particles to be mixed is preferably increased to increase the mixing ratio of the inorganic particles.

In the epoxy composition in accordance with an embodiment of the present invention, the mixing amount of the inorganic particles with respect to the epoxy compound may be appropriately controlled in consideration of the CTE decrease of an epoxy composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total amount of the epoxy compound.

More particularly, in an example embodiment, when the epoxy composition is used as a semiconductor EMC (epoxy molding compound), or the like, the amount of the inorganic particles may be, for example, 30 wt % to 95 wt %, for example, 30 wt % to 90 wt %, without limitation, based on the amount of the epoxy compound in consideration of the CTE value and material processability. In other exemplary embodiments, when the epoxy composition is used as a semiconductor substrate, the amount of the inorganic particles may be 5 wt % to 60 wt %, for example, 10 wt % to 50 wt % based on the total amount of the epoxy compound considering the CTE value and the modulus of the substrate.

Meanwhile, when the fiber is used as the inorganic material, a composite may be obtained by mainly a wetting method of the fiber with the epoxy compound. Thus, the size of the fiber may not be specifically limited. Any kind of fiber commonly used in this field may be used and dimensions thereof are not limited.

Any common fibers used for improving physical properties of a common organic resin cured product may be used without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fibers may include, without limitation, the glass fiber of an E glass fiber, a T glass fiber, an S glass fiber, an NE glass fiber, an E glass fiber, a D glass fiber, a quartz glass fiber, or the like. For example, the glass fiber of E or T may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or in combination of two or more.

When the fiber is used as the filler in the epoxy composition of the present invention, the amount of the fiber may be 10 wt % to 90 wt %, for example, 30 wt % to 70 wt %, in addition, for example, 35 wt % to 65 wt % based on the total weight of the epoxy composition. In the epoxy composition including the fiber, the epoxy composition excluding the fiber may be commonly referred to as a resin component, and in the epoxy composition including the fiber, the amount excluding the fiber may be the resin content. Thus, the resin content may be 10 wt % to 90 wt %, for example, 30 wt % to 70 wt %, in addition, for example, 35 wt % to 65 wt %. The amount of the fiber within the above-described range may be preferred in consideration of the increase in heat resistance and the processability embodiments. The total amount of the epoxy composition means the total weight amounts of all of the constituent components including the epoxy compound, the curing agent, the catalyst, the inorganic material and/or other additives. In addition, as described above, the resin content may include the amounts of all of the constituent components of the epoxy composition including the curing agent, the optional catalyst, the optional inorganic particles and the other additives excluding the fiber.

In the epoxy composition including the fiber provided in the present invention may additionally include inorganic particles as occasion demands. In this case, the inorganic particles may be included by 1 wt % to 70 wt % in the resin content based on the total amount of the resin in consideration of the improvement of the physical properties and processability.

In the epoxy composition, other additives such as a releasing agent, a surface treatment agent, a flame retardant, a plasticizer, bactericides, a leveling agent, a defoaming agent, a colorant, a stabilizer, a coupling agent, a viscosity controlling agent, a diluent, or the like may be mixed to control the physical properties of the epoxy composition within the range of undamaging the physical properties of the epoxy composition as occasion demands.

As described above, the term "epoxy composition" used in the present application is understood to include an epoxy compound of the present invention and other constituents composing the epoxy composition, for example, an optional curing agent, a curing accelerator (catalyst), an inorganic material (filler) (for example, inorganic particles and/or a fiber), other common epoxy compounds, a solvent and other additives mixed as occasion demands in this field. Thus, the "total amount of the epoxy composition" is understood by the total amount of all of the constituents composing the epoxy composition other than the solvent. In general, the solvent may be optionally used to control the amount of the solid content and/or the viscosity of the epoxy composition in consideration of the processability of the epoxy composition, and the like.

The epoxy composition provided in accordance with an example embodiment of the present invention may be used as an electronic material. The electronic material may include, for example, a substrate for semiconductor, a prepreg, a laminate comprising a metal layer placed on the prepreg and a metal layer, a substrate, an encapsulating material (a packaging material), a build-up film, a printed circuit board, or the like. In addition, the epoxy composition may be used in various applications such as an adhesive, a paint composition and a composite material. In accordance with other exemplary embodiments of the present invention, an electronic material including or manufactured by using a composition including the alkoxysilylated isocyanurate epoxy compound of the present invention is provided. Further, a semiconductor apparatus including or manufactured by using the electronic material, may be provided. Particularly, the semiconductor apparatus may be a semiconductor apparatus including a printed circuit board including or manufactured by using the composition including the alkoxysilylated isocyanurate epoxy compound of the present invention (for example, installed with a semiconductor device) and/or may be a semiconductor apparatus including a semiconductor packaging material. In addition, the adhesive, the paint composition or the composite material including or manufactured by using the composition including the alkoxysilylated isocyanurate epoxy compound of the present invention.

In accordance with other exemplary embodiments of the present invention, a cured product including or manufactured by using the epoxy composition provided in accordance with an example embodiment of the present invention may be provided. In the case that applying the epoxy composition provided in an example embodiment of the present invention is practically used, for example, when the epoxy composition is applied as the electronic material, or the like, a cured product formed of the epoxy composition may be used. In this art, the cured product formed of the composition including the epoxy compound and the filler of the inorganic component may be commonly referred to as a composite.

The alkoxysilylated isocyanurate epoxy compound provided in above-described exemplary embodiments of the present invention may show good heat resistance in the composite and/or good flame retardant properties in the cured product.

Particularly, the composite may exhibit a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are good when the CTE value is small, and the lower value of the CTE is not particularly delimited.

For example, a composite including any alkoxysilylated isocyanurate epoxy compound in accordance with exemplary embodiments of the present invention as the epoxy compound, and glass fiber, for example, an E-glass fiber and/or a T-glass fiber as the inorganic material, and having the resin content (the resin content may or may not include inorganic particles) of 30 wt % to 45 wt % may have a CTE of 10 ppm/° C. or less, for example, 8 ppm/° C. or less, for example, 6 ppm/° C. or less, for example, 4 ppm/° C. or less.

In addition, for example, a composite including an alkoxysilylated isocyanurate epoxy compound in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product including an inorganic material) according to the present invention may be higher than 100° C., for example, 130° C. or over, in addition, for example, 250° C. or over. Otherwise, the composite may be Tg-less. The physical properties of the composite is good when the Tg value is large, and the upper value of the Tg is not particularly delimited.

Meanwhile, the cured product formed of the alkoxysilylated isocyanurate epoxy compound itself (a cured product excluding an inorganic material) according to the present invention may have a CTE of 50 ppm/° C. to 150 ppm/° C.

In the present application, the values delimited by the range include the lower limit, the upper limit, any sub ranges in the range, and all numerals included in the range, unless otherwise specifically stated. For example, C1 to C10 is understood to include all of C1, C2, C3, C4, C5, C6, C7, C8, C9 and C10. In addition, in the case when the lower limit or the upper limit of the numerical range is not defined, it would be found that the smaller or the larger value may provide the better properties. In addition, in the case when the limit is not defined, any values may be included. For example, CTE of 4 ppm/° C. or less is understood to include every values in the range such as the CTE of 4, 3.5, 3, 2.7, 2, 1.4, 1, 0.5 ppm/° C., or the like.

Hereinafter, the present invention will be described in detail referring to exemplary embodiments. The following embodiments will be illustrated as examples, but will not limit the present invention.

Synthetic Example 1

Synthesis of Diglycidyl Isocyanurate Having Alkoxysilyl Group (Y2=—CH$_2$—) (Method 1)

(1) Synthesis of a Reaction Intermediate of Diglycidyl Isocyanurate Having an Allyl Group (First Step)

30.0 g of isocyanuric acid (Aldrich), 28 g of allyl bromide (Aldrich), 48 g of potassium carbonate and 773 ml of DMSO were added to a flask and stirred at room temperature for minutes. Then, the temperature increased to 80° C. and reaction was performed overnight. Subsequently, the temperature of the reactant decreased to room temperature, and 129 g of epichlorohydrin and 96 g of potassium carbonate were added and stirred at room temperature for 10 minutes. The temperature increased to 80° C. and maintained for 20 hours. Then, the temperature decreased to room temperature, and worked up after adding 400 ml of ethyl acetate with H$_2$O. MgSO$_4$ was added to an organic layer to remove remaining H$_2$O, and solvents were evaporated to obtain diglycidyl isocyanurate having an allyl group. The NMR data thereof and the reaction scheme of the first step reaction are as follows.

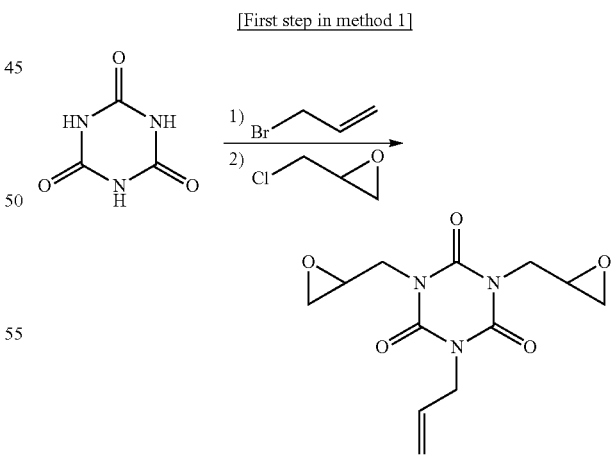

[First step in method 1]

$^1$H NMR (400 MHz, CDCl$_3$): δ=2.68-2.70 (m, 2H), 2.83 (t, J=4.8 Hz, 2H), 3.24-3.28 (m, 2H), 4.01 (dd, J=0.8, 4.8 Hz, 1H), 4.04 (dd, J=0.8, 4.8 Hz, 1H), 4.15 (dd, J=2.4, 5.6 Hz, 1H), 4.19 (dd, J=2.4, 5.6 Hz, 1H), 4.50 (dt, J=1.2, 6.0 Hz, 2H), 5.26 (dd, J=1.2, 10.0 Hz, 1H), 5.34 (dd, J=1.2, 17.2 Hz, 1H), 5.83-5.93 (m, 1H).

(2) Synthesis of Diglycidyl Isocyanurate Having Alkoxysilylating Group (Y2=—CH$_2$—) (Second Step)

7.59 g of monoallyl diglycidyl isocyanurate that is a reaction intermediate obtained in the first step, 6.48 ml of triethoxysilane (Aldrich), 72 mg of platinum oxide, and 150 ml of toluene were put in a 250 ml flask at room temperature. The flask was charged with an argon gas, and the reactant was stirred at 85° C. for 48 hours. Then, the reactant was filtered using a celite filter, and solvents were removed by means of an evaporator to obtain a final product. The NMR data of the final product and the reaction scheme of the second step reaction are as follows.

[Second step in method 1]

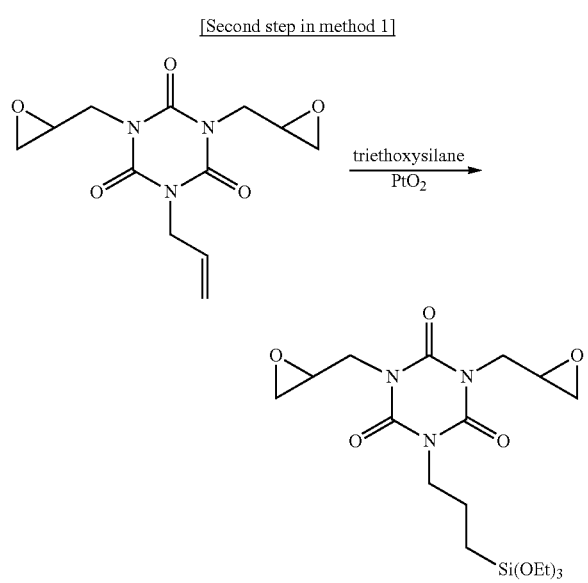

$^1$H NMR (500 MHz, CDCl$_3$): δ=0.61-0.67 (m, 2H), 1.22 (t, J=7.2 Hz, 9H), 1.70-1.80 (m, 2H), 2.68-2.70 (m, 2H), 2.82 (t, J=4.4 Hz, 2H), 3.23-3.27 (m, 2H), 3.79-3.91 (m, 8H), 3.99 (dd, J=0.4, 4.8 Hz, 1H), 4.02 (dd, J=0.4, 4.8 Hz, 1H), 4.15 (dd, J=2.0, 5.2 Hz, 1H), 4.19 (dd, J=2.0, 5.2 Hz, 1H).

Synthetic Example 2

Synthesis of Diglycidyl Isocyanurate Having Alkoxysilyl Group (Y2=—CH$_2$—) (Method 2)

(1) Synthesis of Triallyl Isocyanurate (Alkenylation)

30.0 g of isocyanuric acid (Aldrich), 169 g of allyl bromide (Aldrich), 128 g of potassium carbonate, and 773 ml of DMSO were put in a flask and stirred at room temperature for 10 minutes. Then, the temperature increased to 80° C. and reaction was performed overnight. Subsequently, the temperature of the reactant decreased to room temperature, and worked up after adding 400 ml of ethyl acetate with H$_2$O to remove an inorganic material. MgSO$_4$ was added to an organic layer to remove remaining H$_2$O, and solvents were evaporated to obtain triallyl isocyanurate.

(2) Synthesis of Intermediate of Diglycidyl Isocyanurate Having Allyl Group (First Step)

20.0 g of triallyl isocyanurate obtained in the above (1), 39.57 g of 77 wt % m-CPBA (Aldrich), and 200 ml of methylene chloride were put in a 500 ml flask and stirred at room temperature for 1 day. The reactant was worked up using an aqueous solution of saturated sodium thiosulfite and was extracted using ethyl acetate. Then, the reactant was washed using an aqueous solution of 1N sodium hydroxide and brine, dried using MgSO$_4$, and filtered. Solvents were removed using an evaporator to obtain a reaction intermediate. The reaction scheme of the first step in method 2, and the NMR data of the reaction intermediate thus obtained are as follows. The triallyl isocyanurate was synthesized by the process described in the above (1), however may be purchased to use.

[First step in method 2]

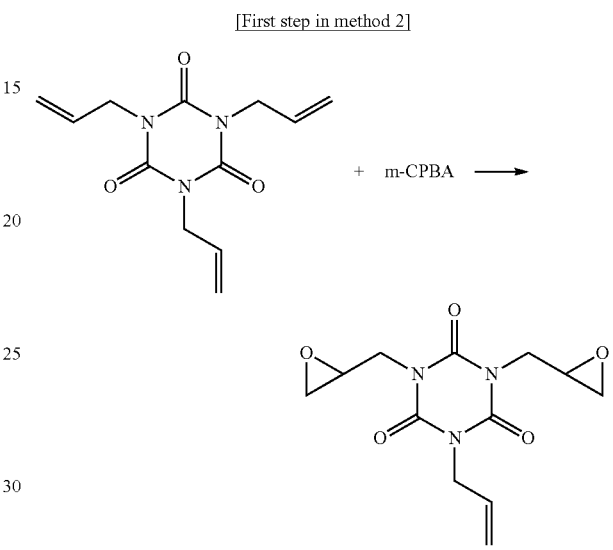

$^1$H NMR (400 MHz, CDCl$_3$): δ=2.68-2.70 (m, 2H), 2.83 (t, J=4.8 Hz, 2H), 3.24-3.28 (m, 2H), 4.01 (dd, J=0.8, 4.8 Hz, 1H), 4.04 (dd, J=0.8, 4.8 Hz, 1H), 4.15 (dd, J=2.4, 5.6 Hz, 1H), 4.19 (dd, J=2.4, 5.6 Hz, 1H), 4.50 (dt, J=1.2, 6.0 Hz, 2H), 5.26 (dd, J=1.2, 10.0 Hz, 1H), 5.34 (dd, J=1.2, 17.2 Hz, 1H), 5.83-5.93 (m, 1H).

(3) Synthesis of Diglycidyl Isocyanurate Having Alkoxysilylating Group (Y2=—CH$_2$—) (Second Step)

7.59 g of monoallyl diglycidyl isocyanurate that is the reaction intermediate obtained in the first step, 6.48 ml of triethoxysilane (Aldrich), 72 mg of platinum oxide, and 150 ml of toluene were put in a 250 ml flask at room temperature. The flask was charged with an argon gas, and the reactant was stirred at 85° C. for 48 hours. Then, the reactant was filtered using a celite filter, and solvents were removed by means of an evaporator to obtain a final product. The NMR data of the final product and the reaction scheme of the second step reaction are as follows.

[Second step in method 2]

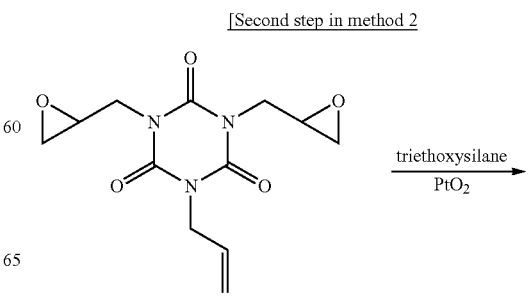

-continued

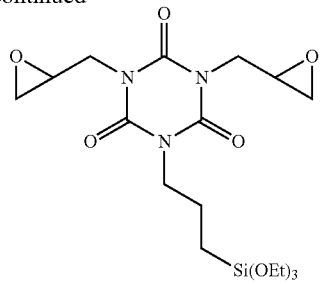

$^1$H NMR (500 MHz, CDCl$_3$): δ=0.61-0.67 (m, 2H), 1.22 (t, J=7.2 Hz, 9H), 1.70-1.80 (m, 2H), 2.68-2.70 (m, 2H), 2.82 (t, J=4.4 Hz, 2H), 3.23-3.27 (m, 2H), 3.79-3.91 (m, 8H), 3.99 (dd, J=0.4, 4.8 Hz, 1H), 4.02 (dd, J=0.4, 4.8 Hz, 1H), 4.15 (dd, J=2.0, 5.2 Hz, 1H), 4.19 (dd, J=2.0, 5.2 Hz, 1H).

Synthetic Example 3

Synthesis of Diglycidyl Isocyanurate Having Alkoxysilyl Group (Y2=—CH$_2$—CH$_2$—) (Method 1)

(1) Synthesis of Intermediate of Diglycidyl Isocyanurate Having Butenyl Group (Y2=—CH$_2$—CH$_2$—) (First Step)

30.0 g of isocyanuric acid (Aldrich), 31 g of butenyl bromide (Aldrich), 48 g of potassium carbonate and 773 ml of DMSO were added to a flask and stirred at room temperature for 10 minutes. Then, the temperature increased to 80° C. and reaction was performed overnight. Subsequently, the temperature of the reactant decreased to room temperature, and 129 g of epichlorohydrin and 96 g of potassium carbonate were added and stirred at room temperature for 10 minutes. The temperature increased to 80° C. and maintained for 20 hours. Then, the temperature decreased to room temperature, and worked up after adding 400 ml of ethyl acetate with H$_2$O to remove an inorganic material and DMSO. MgSO$_4$ was added to an organic layer to remove remaining H$_2$O, and solvents were evaporated to obtain diglycidyl isocyanurate having a butenyl group. The NMR data thereof and the synthetic scheme of the first step are as follows.

[First step in method 1]

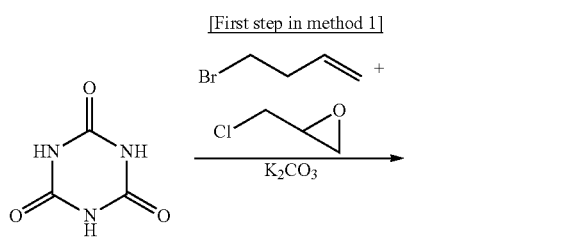

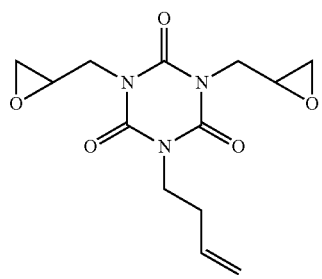

$^1$H NMR (400 MHz, DMSO): δ=2.29 (dd, J=14 Hz, 6.8 Hz, 2H), 2.40 (m, 2H), 2.64 (t, J=4.8 Hz, 2H), 2.95-2.90 (m, 2H), 3.82 (t, J=7.2 Hz, 2H), 3.95-3.83 (m, 4H), 5.09-4.98 (m, 2H), 5.79-5.72 (m, 1H).

(2) Synthesis of Diglycidyl Isocyanurate Having Alkoxysilyl Group (Y2=—CH$_2$CH$_2$—) (Second Step)

10 g of monobutenyl diglycidyl isocyanurate that is the reaction intermediate obtained in the first step, 154 mg of platinum dioxide (Aldrich), 6.68 g of triethoxysilane (TCI), and 200 ml of toluene were added to a flask, and stirred at 80° C. for 17 hours under an argon gas. Then, the reactant was filtered using a celite filter, and the solvent was removed by using an evaporator to obtain a final product. The NMR data of the final compound thus obtained, and the reaction scheme of the second step are as follows.

[Second step in method 1]

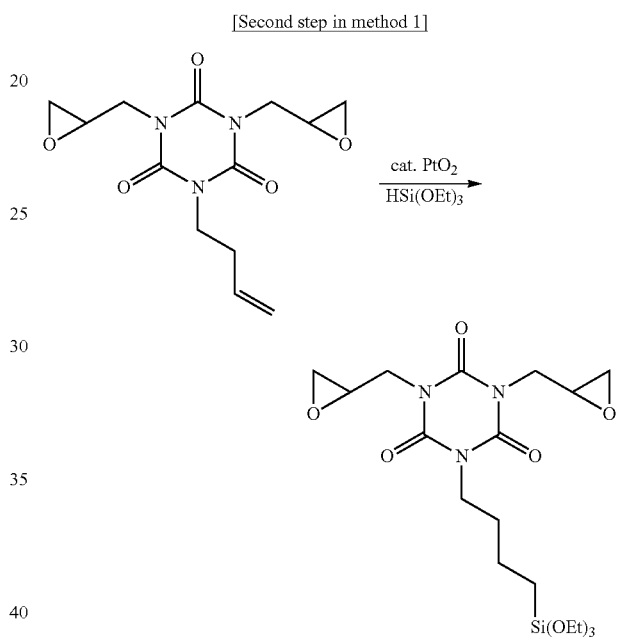

$^1$H NMR (400 MHz, DMSO): δ=0.58 (t, J=8.0 Hz, 2H), 1.17 (t, J=7.0 Hz, 9H), 1.38-1.27 (m, 2H), 1.60-1.52 (m, 2H), 2.40 (m, 2H), 2.63 (t, J=5.2 Hz, 2H), 2.96-2.90 (m, 2H), 3.79-3.77 (m, 8H), 3.95-3.84 (m, 4H).

Synthetic Example 4

Synthesis of Isocyanurate Epoxy Having Alkoxysilyl Group (Y1=—CH$_2$—CH$_2$—, Y2=—CH$_2$—CH$_2$—)

(1) Synthesis of Tributenyl Isocyanurate (Alkenylation)

30.0 g of isocyanuric acid (Aldrich), 106 ml (141 g) of butenyl bromide (Aldrich), 128 g of potassium carbonate and 773 ml of DMSO were added to a flask and stirred at room temperature for 10 minutes. Then, the temperature increased to 80° C. and reaction was performed overnight. Subsequently, the temperature of the reactant decreased to room temperature, and the reactant was worked up after adding 400 ml of ethyl acetate with H$_2$O to remove an inorganic material and DMSO. MgSO$_4$ was added to an organic layer to remove remaining H$_2$O, and solvents were evaporated to obtain tributenyl isocyanurate. The NMR data thereof and the synthetic scheme of the alkenylation are as follows.

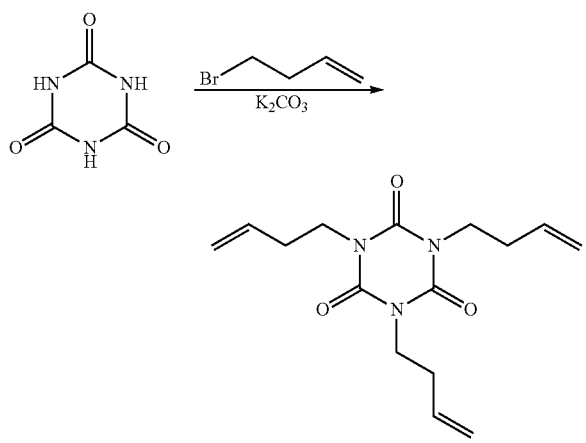

¹H NMR (400 MHz, DMSO): δ=2.28 (dd, J=14 Hz, 6.8 Hz, 6H), 3.82 (t, J=7.2 Hz, 6H), 5.08-4.98 (m, 6H), 5.80-5.72 (m, 3H).

(2) Synthesis of Isocyanurate-Based Epoxy Intermediate Having Butenyl Group (First Step)

66.0 g of tributenyl isocyanurate synthesized in the above (1), 50.5 g of m-CPBA (Aldrich), 41.8 g of sodium hydrogen carbonate, and 750 ml of chloroform were put in a flask and stirred at room temperature for 12 hours. After finishing the stirring, 50.5 g of m-CPBA was further added and stirred at room temperature for 6 hours. Then, 600 ml of ethyl acetate was added, washed three times using an aqueous 1N NaOH solution. An organic layer was washed using a saturated NaCl aqueous solution at least one time, and moisture in the organic layer was removed using MgSO₄. Then solvents in the organic layer were evaporated to obtain an isocyanurate-based epoxy intermediate having a butenyl group. The NMR data of the reaction intermediate thus obtained, and the reaction scheme of the first step are as follows.

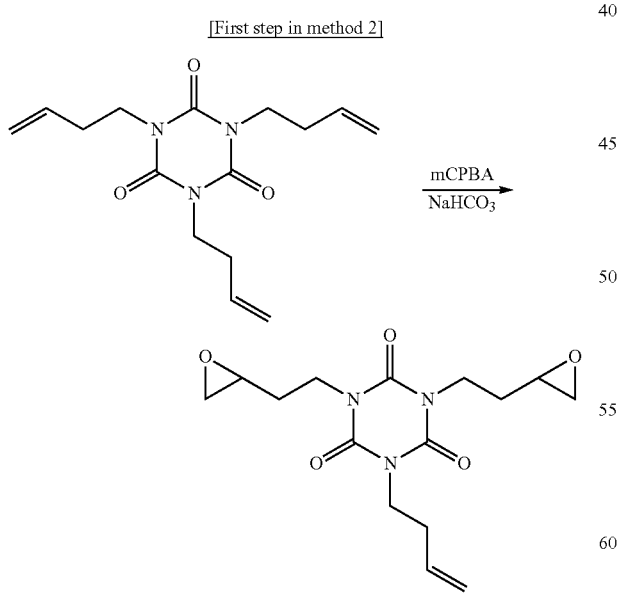

¹H NMR (400 MHz, DMSO): δ=1.86-1.60 (m, 4H), 2.30 (dd, J=14 Hz, 6.8 Hz, 2H), 2.40 (m, 2H), 2.64 (t, J=4.8 Hz, 2H), 2.96-2.90 (m, 2H), 3.82 (t, J=6.8 Hz, 2H), 3.94-3.84 (m, 4H), 5.08-4.99 (m, 2H), 5.80-5.72 (m, 1H).

(3) Synthesis of Isocyanurate-Based Epoxy Having Alkoxysilyl Group (Y1=—CH₂—CH₂—, Y2=—CH₂—CH₂—) (Second Step)

6.4 g of the isocyanurate-based epoxy intermediate having a butenyl group obtained in the first step, 100 mg of platinum dioxide (Aldrich), 2.6 ml of triethoxysilane (TCI) and 100 ml of toluene were put in a flask and stirred at 80° C. for 17 hours under an argon gas. Then, the temperature decreased to room temperature, and reactant was filtered using a celite filter to remove platinum dioxide. Subsequently, organic solvents of a filtrate were evaporated to obtain a final product. The NMR data of the final product, and the reaction scheme of the second step are as follows.

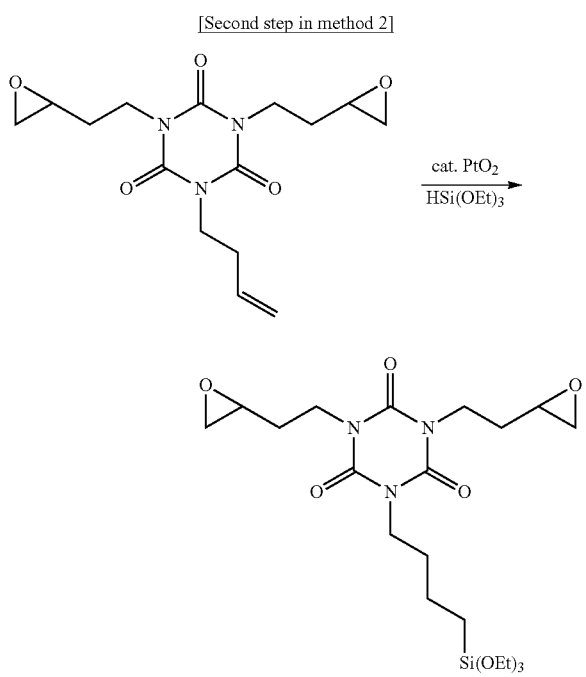

¹H NMR (400 MHz, DMSO): δ=0.57 (t, J=8.0 Hz, 2H), 1.15 (t, J=7.0 Hz, 9H), 1.38-1.27 (m, 2H), 1.60-1.52 (m, 2H), 1.87-1.61 (m, 4H), 2.40 (m, 2H), 2.63 (t, J=5.2 Hz, 2H), 2.96-2.90 (m, 2H), 3.79-3.77 (m, 8H), 3.83-3.79 (m, 4H).

Synthetic Example 5

Synthesis of Diglycidyl Isocyanurate Having Alkylsilyl Group 2.85 g of the monoallyl diglycidyl isocyanurate obtained in the first step of Example 1, 4.85 ml of triethylsilane (TCI), 69.0 mg of platinum oxide and 150 ml of toluene were put in a 250 ml flask. The flask was charged with an argon gas, and the reactant was stirred at 85° C. for 7 days. Then, the reactant was filtered using a celite filter, and solvents were removed by using an evaporator to obtain alkylsilylated diglycidyl isocyanurate. The NMR data of the compound thus obtained, and the reaction scheme thereof are as follows.

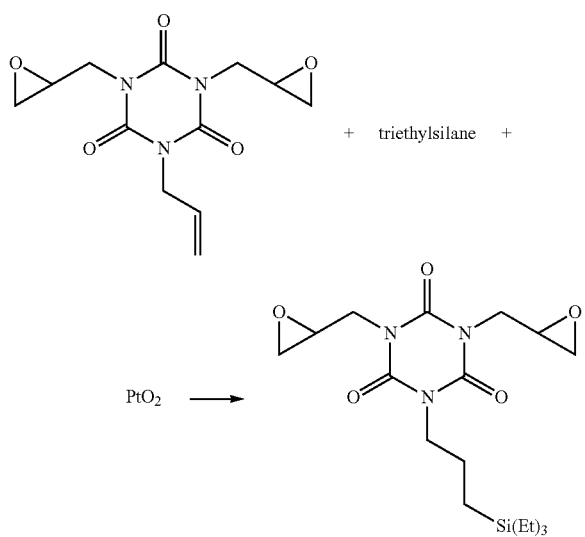

$^1$H NMR (500 MHz, CDCl$_3$): δ=0.49-0.55 (m, 8H), 0.92 (t, J=7.8 Hz, 9H), 1.59-1.67 (m, 2H), 2.68-2.70 (m, 2H), 2.82 (t, J=4.4 Hz, 2H), 3.23-3.27 (m, 2H), 3.86 (t, J=7.8 Hz, 2H), 3.99 (dd, J=0.4, 4.8 Hz, 1H), 4.02 (dd, J=0.4, 4.8 Hz, 1H), 4.15 (dd, J=2.0, 5.2 Hz, 1H), 4.19 (dd, J=2.0, 5.2 Hz, 1H).

Evaluation of Physical Properties: Manufacturing of Cured Product and Evaluation of Heat-Resistance 1. Manufacturing of Epoxy Cured Product An epoxy compound, a curing agent (a phenol curing agent (HF-1M™, Meiwa Plastic Industries, Ltd., 107 eq.) or an amine curing agent (4,4'-diaminodiphenylmethane, DDM, Aldrich)) and triphenyl phosphine (purchased from Aldrich) as a curing catalyst (in the case when added) were dissolved in methyl ethyl ketone by the mixing amounts as illustrated in the following Table 1 so that the solid content was 40 wt %, and were mixed to obtain a homogeneous solution to obtain a mixture solution (the solid content represents the amount of solid phase materials in the mixture solution). Then, the mixture solution was put in a heated vacuum oven at 100° C. to remove solvents, and was cured in a preheated hot press to manufacture an epoxy cured product (4 mm×16 mm×0.1 mm).

2. Manufacturing of Composite (Cured Product) Including Epoxy Compound and Glass Fiber An epoxy compound, a curing agent (a phenol curing agent (HF-1M™, Meiwa Plastic Industries, Ltd., 107 eq.) or an amine curing agent (4,4'-diaminodiphenylmethane, DDM, Aldrich)) and triphenyl phosphine (TPP, purchased from Aldrich) as a curing catalyst (in the case when added) were dissolved in methyl ethyl ketone by the mixing amounts as illustrated in the following Table 2 so that the solid content was 40 wt %, and were mixed to obtain a homogeneous solution. Into the mixture thus obtained, a glass fiber (glass fiber fabric by Nittobo Co., E-glass 2116) was impregnated to manufacture a glass fiber composite including the epoxy compound. Then, the composite was inserted into a heated vacuum oven at 100° C. to remove solvents, and was cured in a preheated hot press to manufacture a glass fiber composite film (4 mm×16 mm×0.1 mm) according to Examples 5 to 10 and Comparative Examples 3 to 5. While manufacturing the composite film, the resin content of the composite film was controlled according to the pressure of a press and the viscosity of a resin, and the amount of the resin in the composite film is illustrated in the following Table 2.

3. Manufacturing of Composite (Cured Product) Including Epoxy Compound, Glass Fiber and Silica An epoxy compound and a silica slurry (solid content 70 wt %, 2-methoxyethanol solvent, the distribution of the particle size of silica is from 450 nm to 3 μm) were dissolved in methyl ethyl ketone by the mixing amounts as illustrated in the following Table 2 so that the solid content was 40 wt %. The mixture solution thus obtained was mixed at the rate of 1,500 rpm for 1 hour, and a phenol curing agent (HF-1M™ (Meiwa Plastic Industries, Ltd., 107 eq.)) was added and additional mixing was conducted for 50 minutes. And then, triphenyl phosphine (Aldrich) was finally added as a curing catalyst and mixed for 10 minutes further to obtain an epoxy mixture. Into the epoxy mixture thus obtained, a glass fiber (glass fiber fabric of Nittobo Co., E-glass 2116) was impregnated to manufacture a glass fiber composite including the epoxy compound. Then, the composite was inserted into a heated vacuum oven at 100° C. to remove the solvent, and was cured in a preheated hot press to manufacture a glass fiber composite film (4 mm×16 mm×0.1 mm) according to Examples 11 to 13. While manufacturing the composite film, the resin content of the composite film was controlled according to the pressure of a press and the viscosity of a resin, and the amount of the resin in the composite film is illustrated in the following Table 2.

4. Manufacturing of Composite (Cured Product) Including Epoxy Compound and Silica An epoxy compound and a silica slurry (solid content 70 wt %, 2-methoxyethanol solvent, the distribution of the particle size of silica is from 450 nm to 3 μm) were dissolved in methyl ethyl ketone by the mixing amounts as illustrated in the following Table 3 so that the solid content was 40 wt %. The mixture solution thus obtained was mixed at the rate of 1,500 rpm for 1 hour, and a phenol curing agent (HF-1M™ (Meiwa Plastic Industries, Ltd., 107 eq.)) was added and additional mixing was conducted for 50 minutes. And then, triphenyl phosphine (Aldrich) was finally added as a curing catalyst and mixed for 10 minutes further to obtain an epoxy mixture. Then, the mixture was inserted into a heated vacuum oven at 100° C. to remove the solvent, and was cured in a preheated hot press to manufacture an epoxy composite (5 mm×5 mm×3 mm) according to Examples 14 to 18 and Comparative Examples 6 and 7.

5. Evaluation of Physical Properties (1) Evaluation of Heat-Resistant Properties The dimensional changes with respect to the temperatures of the cured products obtained in the Examples and Comparative Examples in Tables 1 to 3 were evaluated by using a Thermo-mechanical analyzer (Film/fiber mode, Force 0.1 N) and are illustrated in the following Tables 1 to 3. The samples of the epoxy cured product and the silica composite were manufactured in a size of 5×5×3 (mm$^3$) (expansion mode), and the samples of the glass fiber composite films were manufactured in a size of 4×16×0.1 (mm$^3$) (tension mode). In addition, the thermal decomposition temperatures of the cured products were evaluated by using a thermogravimetric analyzer (TGA).

TABLE 1

Epoxy resin cured product

| | Epoxy mixture composition | | | | | | | Heat-resistance | |
|---|---|---|---|---|---|---|---|---|---|
| | Epoxy compounds (g) | | | | HF-IM curing agent (g) | TPP curing catalyst (g) | DDM curing agent (g) | CTE (ppm/° C.) | Tg (° C.) |
| No. | Syn. Exam. 1 or 2 | Isocyanurate epoxy[(1)] | Bisphenol A epoxy[(3)] | Aminophenol epoxy[(4)] | | | | | |
| Exam. 1 | 5.00 | — | — | — | — | — | 1.10 | 112 | Tg-less |
| Exam. 2 | 5.00 | — | — | — | 2.35 | 0.05 | — | 85 | 155 |
| Exam. 3 | 4.50 | — | 0.50 | — | 2.44 | 0.05 | — | 98 | 140 |
| Exam. 4 | 4.50 | — | — | 0.50 | 2.69 | 0.05 | — | 93 | 155 |
| Com. Exam. 1 | | 5.0 | | | — | — | 2.50 | 50 | 170 |
| Com. Exam. 2 | | 5.0 | | | 5.40 | 0.05 | — | Crack forming-unmeasurable | |

TABLE 2

Epoxy glass fiber composite

| | Epoxy mixture composition | | | | | | | | | | | | Heat-resistance | |
|---|---|---|---|---|---|---|---|---|---|---|---|---|---|---|
| | Epoxy compounds (g) | | | | | | | HF-IM curing agent (g) | TPP curing catalyst (g) | DDM curing agent (g) | Silica (g) | Resin amount (wt %) | CTE (ppm/° C.) | Tg (° C.) |
| No. | Syn. Exam. 1 or 2 | Syn. Exam. 3 | Syn. Exam. 4 | Isocyanurate epoxy[(1)] | Syn. Exam. 5[(2)] | Bisphenol A epoxy[(3)] | Aminophenol epoxy[(4)] | | | | | | | |
| Exam. 5 | 5.00 | | | — | — | — | — | — | — | 2.50 | — | 40 | 7.6 | Tg-less |
| Exam. 6 | 5.00 | | | — | — | — | — | 2.40 | 0.05 | — | — | 40 | 7.6 | Tg-less |
| Exam. 7 | 5.00 | | | — | — | — | — | 2.40 | 0.05 | — | — | 35 | 5.8 | Tg-less |
| Exam. 8 | 5.00 | | | — | — | — | — | 2.36 | 0.05 | — | — | 38 | 7.7 | Tg-less |
| Exam. 9 | 4.50 | | | — | — | 0.5 | — | 2.44 | 0.05 | — | — | 39 | 5.7 | Tg-less |
| Exam. 10 | 4.50 | | | — | — | — | 0.5 | 2.69 | 0.05 | — | — | 35 | 7.6 | Tg-less |
| Exam. 11 | 5.00 | | | — | — | — | — | 2.41 | 0.05 | — | 0.50 | 37 | 7.5 | Tg-less |
| Exam. 12 | — | 5 | | — | — | — | — | 2.33 | 0.048 | — | 1.00 | 37 | 7.8 | Tg-less |
| Exam. 13 | — | | 5 | — | — | — | — | 2.63 | 0.054 | — | 1.00 | 36 | 8.0 | Tg-less |
| Com. Exam. 3 | — | — | — | 5.00 | — | — | — | — | — | 2.50 | — | 39 | 9.0 | 140 |
| Com. Exam. 4 | — | — | — | 5.00 | — | — | — | 5.40 | 0.05 | — | — | 45 | 15.8 | 210 |
| Com. Exam. 5 | — | — | — | — | 5 | — | — | 2.69 | 0.05 | — | — | 34 | 16.3 | 150 |

TABLE 3

Epoxy inorganic particle composite

| | Epoxy mixture composition | | | | | | | HF-IM curing agent (g) | TPP curing catalyst (g) | Silica (g) | Silica amount (wt %) | Heat-resistance | |
|---|---|---|---|---|---|---|---|---|---|---|---|---|---|
| | Epoxy compounds (g) | | | | | | | | | | | CTE (ppm/° C.) | Tg (° C.) |
| No. | Syn. Exam. 1 or 2 | Syn. Exam. 3 | Syn. Exam. 4 | Isocyanurate epoxy[(1)] | Syn. Exam. 5[(2)] | Bisphenol A epoxy[(3)] | Aminophenol epoxy[(4)] | | | | | | |
| Exam. 14 | 5.00 | — | — | — | — | — | — | 2.32 | 0.05 | 29.48 | 80 | 6.5 | Tg-less |

TABLE 3-continued

Epoxy inorganic particle composite

| | Epoxy mixture composition | | | | | | | | | | | Heat-resistance | |
|---|---|---|---|---|---|---|---|---|---|---|---|---|---|
| | Epoxy compounds (g) | | | | | | | HF-IM | TPP | | | | |
| No. | Syn. Exam. 1 or 2 | Syn. Exam. 3 | Syn. Exam. 4 | Isocyanurate epoxy[1] | Syn. Exam. 5[2] | Bisphenol A epoxy[3] | Aminophenol epoxy[4] | curing agent (g) | curing catalyst (g) | Silica (g) | Silica amount (wt %) | CTE (ppm/°C.) | Tg (°C.) |
| Exam. 15 | — | 5.00 | — | — | — | — | — | 2.33 | 0.048 | 29.32 | 80 | 7.0 | Tg-less |
| Exam. 16 | — | — | 5.00 | — | — | — | — | 2.63 | 0.054 | 30.52 | 80 | 7.5 | Tg-less |
| Exam. 17 | 4.50 | — | — | — | — | 0.5 | — | 2.44 | 0.05 | — | 80 | 7.6 | Tg-less |
| Exam. 18 | 4.50 | — | — | — | — | — | 0.5 | 2.69 | 0.05 | — | 80 | 9.0 | Tg-less |
| Com. Exam. 6 | — | — | — | 5.00 | — | — | — | 5.40 | 0.05 | 41.80 | 80 | Crack forming-unmeasurable | |
| Com. Exam. 7 | — | — | — | — | — | 5.00 | — | 2.84 | 0.05 | 31.55 | 80 | 15.9 | 110 |

Note: The epoxy compounds used in Tables 1, 2 and 3 are as follows.

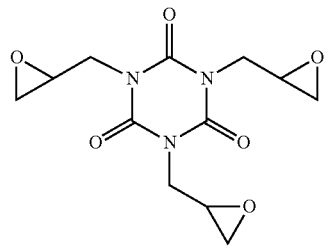

(1) Isocyanurate epoxy

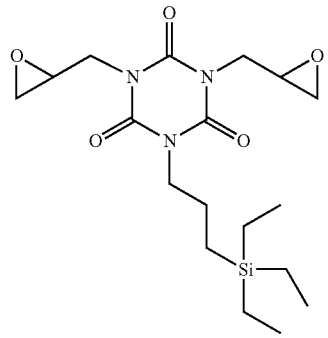

(2) Isocyanurate epoxy having an alkylsilyl group

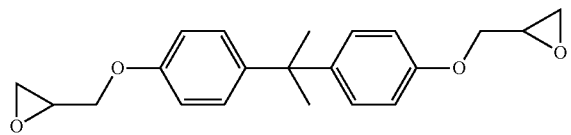

(3) Bisphenyl A-based epoxy

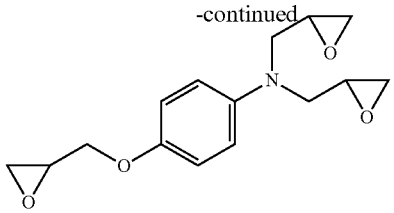

(4) Aminophenol-based epoxy

The cured product formed of the alkoxysilylated isocyanurate epoxy compound itself according to the present invention showed an increased CTE and a decreased Tg as compared to the cured product formed from the isocyanurate epoxy compound itself excluding the alkoxysilyl group. However, on the contrary, the composite of the alkoxysilylated isocyanurate epoxy compound according to the present invention showed decreased CTE and higher Tg or Tg-less levels, as compared to the composite of the isocyanurate epoxy compound excluding the alkoxysilyl group.

Particularly, as shown in Table 1 and FIG. 1, the cured product formed of the alkoxysilylated isocyanurate epoxy compound itself of Formula 1 (Example 1) according to the present invention had a significantly increased CTE as compared to the cured product formed of the epoxy compound itself having the same core structure but excluding the alkoxysilyl group (Comparative Example 1). However, the CTE of the composite of the alkoxysilylated isocyanurate epoxy compound obtained through making the composites with the glass fiber (Examples 5 to 13) was 5.8 to 8 ppm/°C., which was very low as compared to the CTE of 9 to 16 ppm/°C. of the composite of the isocyanurate epoxy compound excluding the alkoxysilyl group (Comparative Examples 3 to 5).

Figure 2:
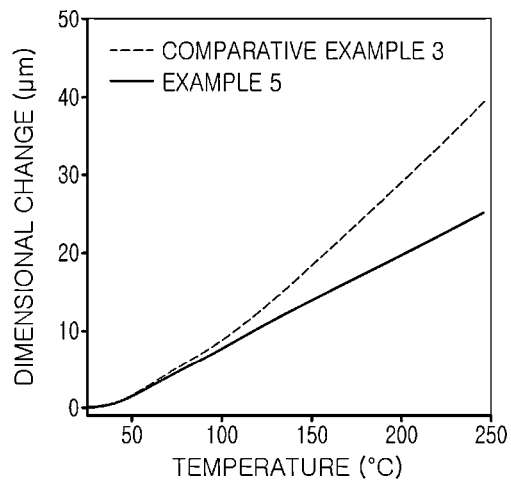
FIG. 2 is a graph illustrating dimensional changes with respect to the change of a temperature according to the composites of Example 5 and Comparative Example 3.
Figure 3:
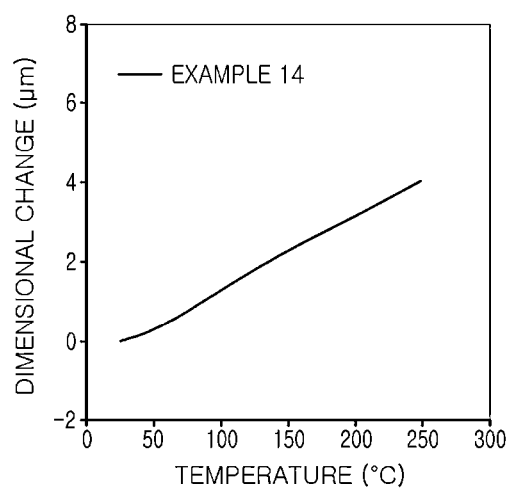
FIG. 3 is a graph illustrating dimensional change with respect to the change of a temperature according to the composite of Example 14.

As illustrated in FIG. 2, the CTE of the composite according to Example 5 was even smaller than the CTE of the composite according to Comparative Example 3. As shown in Tables 1 and 2, Tg-less was observed for the composite according to Example 5, and a glass transition temperature was observed around 140° C. for the composite according to Comparative Example 3.

As described above, it would be found that the composite of the alkoxysilylated isocyanurate epoxy compound of Formula 1 according to the present invention showed a decreased CTE and an increased Tg (or Tg-less) as compared to the composite of the isocyanurate epoxy compound excluding the alkoxysilyl group, and heat-resistant properties were improved.

Meanwhile, the CTE value of the epoxy composite highly filled with inorganic particles according to Example 14 was 6.5 ppm/° C., which was even smaller than the CTE value of the bisphenol epoxy composite excluding the alkoxysilyl group according to Comparative Example 7. In addition, the glass transition temperature was also Tg-less and good heat-resistance was shown. For the comparison with Example 14, an isocyanurate epoxy composite excluding the alkoxysilyl group highly filled with the inorganic particles was manufactured in Comparative Example 6. However, crack was formed, and the physical properties could not be evaluated. Thus, the comparison was conducted with respect to Comparative Example 7.

The decrease of CTE and the increase of Tg or the Tg-less properties of the alkoxysilylated isocyanurate epoxy composite are considered to be obtained due to the improvement of the bonding properties of the epoxy compound and the filler in the composite.

Figure 4A:
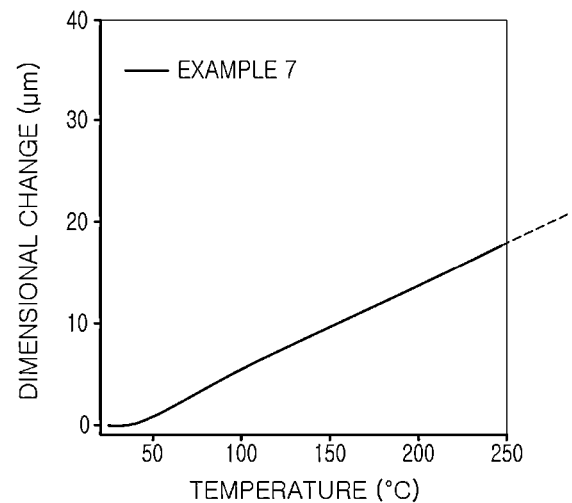
FIG. 4A is a graph illustrating dimensional change with respect to the change of a temperature according to the composite of Example 7.
Figure 4B:
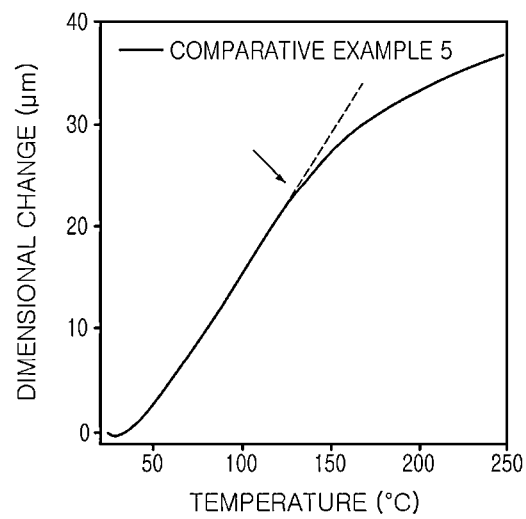
FIG. 4B is a graph illustrating dimensional change with respect to the change of a temperature according to the composite of Comparative Example 5.

In addition, as shown in FIGS. 4A and 4B and Table 2, the CTE of the alkoxysilylated isocyanurate epoxy composite (Example 7) was 5.8 ppm/° C., which was very good as compared to the CTE=16 ppm/° C. of the isocyanurate epoxy composite having an alkylsilyl group (Comparative Example 5). The CTE of the Comparative Example 5 was the CTE value of a general epoxy composite. From the results, it would be found that the heat-resistant properties of the epoxy composite according to the present invention were improved due to the alkoxysilyl group.

Figure 5A:
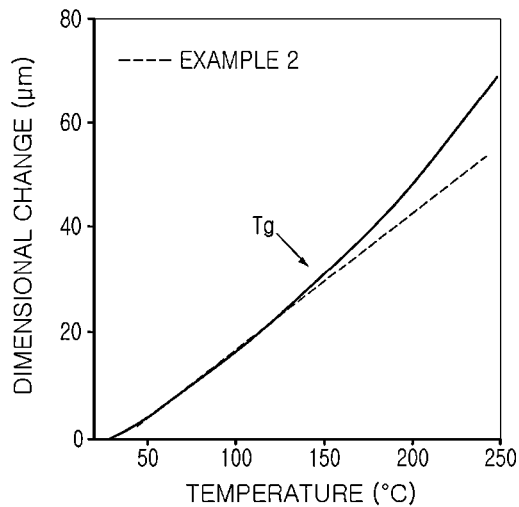
FIG. 5A is a graph illustrating dimensional change with respect to the change of a temperature according to the composite of Example 2.
Figure 5B:
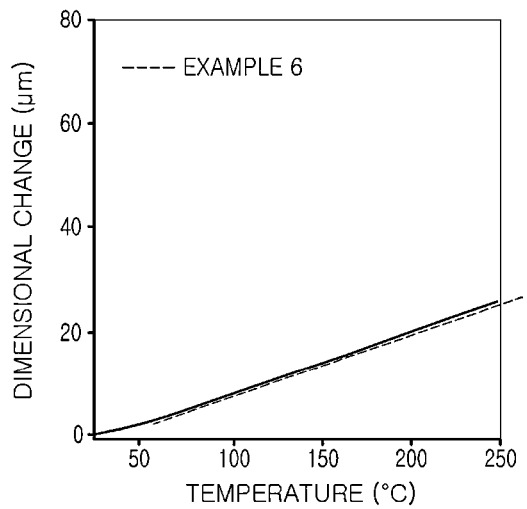
FIG. 5B is a graph illustrating dimensional change with respect to the change of a temperature according to the composite of Comparative Example 6.

Further, the Tg of the isocyanurate epoxy composite having an alkoxysilyl group was observed to be increased as compared to the Tg of the cured product formed of the epoxy composite itself. For example, as shown in FIGS. 5A and 5B, the glass transition temperature of the epoxy cured product according to Example 2 was observed around 155° C., however the epoxy composite according to Example 6 exhibited Tg-less and had significantly improved heat-resistant properties. The change of the glass transition temperature thus explained seems to be due to the effective formation of a bonding between boundaries of the alkoxysilyl group with the glass fiber.

(2) Evaluation of Thermal Decomposition Temperature

The thermal decomposition temperatures of the epoxy cured product according to Example 2, the epoxy composite according to Example 6, the epoxy cured product according to Comparative Example 1, and the epoxy composite of Comparative Example 3 were measured and are illustrated in the following Table 4 and FIGS. 6 and 7.

TABLE 4

| | Thermal decomposition temperature | |
|---|---|---|
| | Comparative Examples | Examples |
| Epoxy cured product | 372° C. (Comparative Example 1) | 464° C. (Example 2) |
| Epoxy composite | 373° C. (Comparative Example 3) | 479° C. (Example 6) |

Figure 6A:
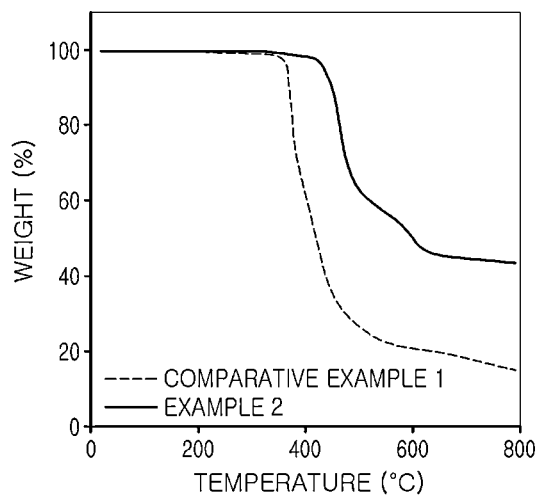
FIG. 6A is a graph illustrating wt % changes with respect to the change of a temperature according to the composites of Example 2 and Comparative Example 1.
Figure 6B:
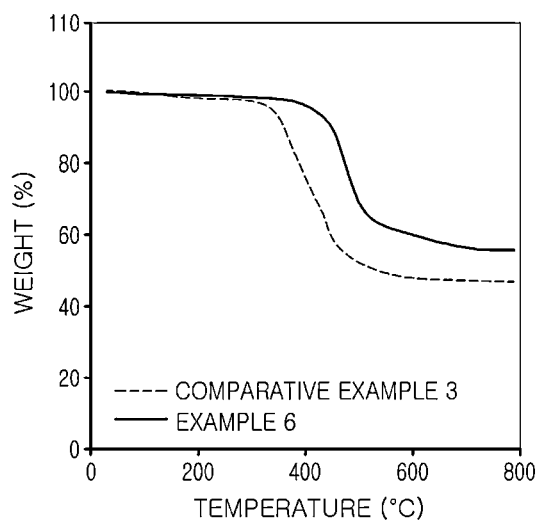
FIG. 6B is a graph illustrating wt % changes with respect to the change of a temperature according to the composites of Example 6 and Comparative Example 3.

In FIG. 6A, the wt % changes with respect to the change of a temperature according to Example 2 and Comparative Example 1 are illustrated, and in FIG. 6B, the wt % changes with respect to the change of a temperature according to Example 6 and Comparative Example 3 are illustrated. In addition, in FIG. 7A, the wt % changes with respect to the change of a temperature according to Example 2 and Example 6 are illustrated, and in FIG. 7B, the wt % changes with respect to the change of a temperature according to Comparative Example 1 and Comparative Example 3 are illustrated.

As shown in Table 4 and FIGS. 6 and 7, the cured product and the composite of the isocyanurate epoxy compound having an alkoxysilyl group according to the present invention had higher thermal decomposition temperatures than the cured product and the composite of the isocyanurate epoxy compound excluding the alkoxysilyl group. Particularly, the thermal decomposition temperature of Example 2 was higher than Comparative Example 1 by 92° C., and the thermal decomposition temperature of Example 6 was higher than Comparative Example 3 by 106° C.

As described above, the isocyanurate epoxy compound having an alkoxysilyl group showed higher thermal decomposition temperature than that of the isocyanurate epoxy compound excluding the alkoxysilyl group, and it would be found that the heat resistance properties were improved through the alkoxysilylation.

Figure 7A:
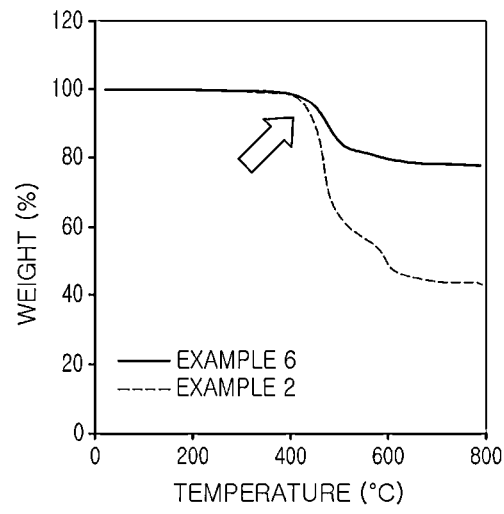
FIG. 7A is a graph illustrating wt % changes with respect to the change of a temperature according to the composites of Example 2 and Example 6.
Figure 7B:
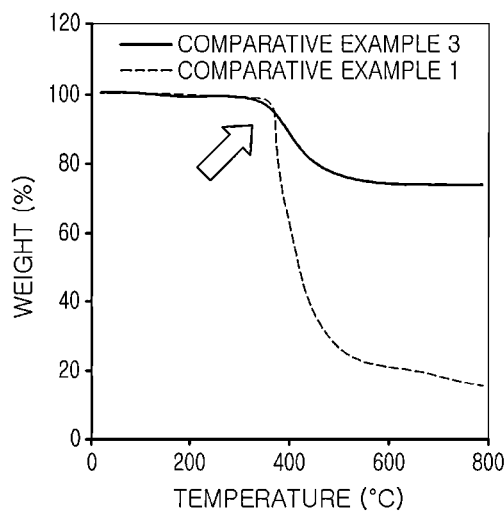
FIG. 7B is a graph illustrating wt % changes with respect to the change of a temperature according to the composites of Comparative Example 1 and Comparative Example 3.

As shown in Table 3 and FIGS. 7A and 7B, the increase of the thermal decomposition temperature of a system was observed for the isocyanurate epoxy system having an alkoxysilyl group (Example 6) due to the composite different from the isocyanurate epoxy system excluding the alkoxysilyl group (Comparative Example 3). This result is considered to be obtained due to the improvement of a bonding between boundaries of the alkoxysilyl group with the filler through making the composites.

(3) Evaluation of Flame Retardant Properties

Figure 8:
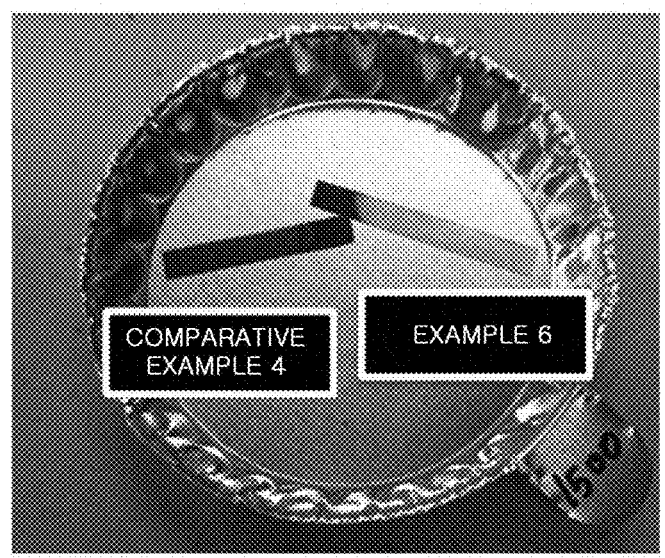
FIG. 8 is a photographic image illustrating extinguished composite films according to Example 6 and Comparative Example 4, after combustion.

Strips of the composites according to Example 6 and Comparative Example 4 were ignited, and photographic images of the burned strips are illustrated in FIG. 8. As illustrated in FIG. 8, all of the strips of the composites according to Example 6 and Comparative Example 4 were naturally extinguished within 1 to 2 seconds after the ignition and showed good flame retardant properties. That is, the isocyanurate core had a structure including nitrogen, and had good flame retardant properties. Thus, the alkoxysilylated isocyanurate epoxy compound according to the present invention had good flame retardant properties as well as the common isocyanurate epoxy compound unmodified and excluding an alkoxysilyl group. The composite of the alkoxysilylated isocyanurate epoxy compound according to the present invention also exhibited good flame retardant properties.

While the present invention has been shown and described in connection with the exemplary embodiments, it will be apparent to those skilled in the art that modifications and variations can be made without departing from the spirit and scope of the invention as defined by the appended claims.

The invention claimed is:

1. An epoxy composition comprising:
   an isocyanurate epoxy compound having an alkoxysilyl group of following Formula 1:

[Formula 1]

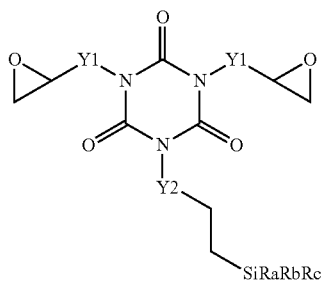

in Formula 1, Y1 and Y2 are independently selected from the group consisting of a C1-C10 alkanediyl, a C6-C10 aryldiyl and a C7-C10 arylated alkanediyl group and are the same or different, the alkanediyl group is linear or branched and cyclic or acyclic, and the alkanediyl, the aryldiyl and the arylated alkanediyl group does or does not include a heteroatom of N, O, S or P, at least one of $R_a$ to $R_c$ is a C1-C10 alkoxy group, and the remainders thereof are a C1-C10 alkyl, a C6-C10 aryl, or a C7-C10 aralkyl group, the alkyl group and the alkoxy group are linear or branched and cyclic or acyclic, and the alkyl, the alkoxy, the aryl and the aralkyl group does or does not include a heteroatom of N, O, S or P;

a curing agent for the isocyanurate epoxy compound having an alkoxysilyl group of Formula 1; and at least one filler selected from inorganic particles and fibers.

2. The epoxy composition of claim 1, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

3. The epoxy composition of claim 2, wherein the epoxy compound comprises bisphenol A, bisphenol F, bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic or a novolak unit, as a core structure.

4. The epoxy composition of claim 1, wherein the inorganic particle is at least one selected from the group consisting of silica, zirconia, titania, alumina, silicon nitride, aluminum nitride, ladder silsesquioxane and cage silsesquioxane.

5. The epoxy composition of claim 1, wherein an amount of the inorganic particles is 5 wt % to 95 wt % based on a total amount of the epoxy composition.

6. The epoxy composition of claim 1, wherein an amount of the inorganic particles is 1 wt % to 70 wt % based on a total amount of a resin.

7. The epoxy composition of claim 1, wherein the fiber is at least one selected from the group consisting of a glass fiber selected from the group consisting of an E glass fiber, a T glass fiber, an S glass fiber, an NE glass fiber, a D glass fiber and a quartz glass fiber, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber.

8. The epoxy composition of claim 1, wherein an amount of the fiber is 10 wt % to 90 wt % based on a total amount of the epoxy composition.

9. An electronic material comprising the epoxy composition according to claim 1.

10. A prepreg comprising the epoxy composition according to claim 1.

11. A laminate comprising a metal layer placed on the prepreg of claim 10.

12. A substrate comprising the epoxy composition according to claim 1.

13. A film comprising the epoxy composition according to claim 1.

14. A printed circuit board comprising the prepreg of claim 10.

15. A semiconductor device comprising the printed circuit board of claim 14.

16. A semiconductor packaging material comprising the epoxy composition according to claim 1.

17. A semiconductor device comprising the semiconductor packaging material of claim 16.

18. An adhesive comprising the epoxy composition according to claim 1.

19. A paint composition comprising the epoxy composition according to claim 1.

20. A composite material comprising the epoxy composition according to claim 1.

21. A cured product of the epoxy composition according to claim 1.

22. The cured product of the epoxy composition of claim 21, wherein the cured product has a coefficient of thermal expansion of 15 ppm/° C. or less.

23. The cured product of the epoxy composition of claim 21, wherein the cured product has a glass transition temperature of 100° C. or over, or not exhibiting the glass transition temperature.

24. The cured product of the epoxy composition of claim 21, wherein the cured product has a coefficient of thermal expansion of 50 ppm/° C. to 150 ppm/° C.

* * * * *